United States Patent [19]
Lundquist

[11] Patent Number: 5,477,856
[45] Date of Patent: Dec. 26, 1995

[54] TORQUABLE CATHETER AND TORQUABLE TUBULAR MEMBER FOR USE THEREWITH

[76] Inventor: Ingemar H. Lundquist, 17 Mile Drive at The Dunes, Pebble Beach, Calif. 93953-1186

[21] Appl. No.: 217,383

[22] Filed: Mar. 24, 1994

Related U.S. Application Data

[62] Division of Ser. No. 126,681, Sep. 24, 1993, Pat. No. 5,329,923, which is a continuation of Ser. No. 945,666, Sep. 16, 1992, abandoned, which is a continuation-in-part of Ser. No. 790,648, Nov. 8, 1991, abandoned, which is a continuation-in-part of Ser. No. 725,660, Jul. 3, 1991, abandoned, which is a continuation-in-part of Ser. No. 657,106, Feb. 15, 1991, abandoned.

[51] Int. Cl.$^6$ ........................................................ A61B 5/04
[52] U.S. Cl. ........................... 128/642; 607/122; 604/281
[58] Field of Search .................................. 128/4, 6, 642, 128/772–774; 607/116, 119, 122, 125–128; 604/94, 95, 280, 282; 74/607

[56] References Cited

U.S. PATENT DOCUMENTS

| | | | |
|---|---|---|---|
| 4,911,148 | 3/1990 | Sosnowski et al. | 128/4 X |
| 4,998,923 | 3/1991 | Samson et al. | 606/194 |
| 5,284,128 | 2/1994 | Hart | 128/4 |
| 5,329,923 | 7/1994 | Lundquist | 128/642 |

Primary Examiner—William E. Kamm
Assistant Examiner—Jeffrey R. Jastrzab
Attorney, Agent, or Firm—Flehr, Hohbach, Test, Albritton & Herbert

[57] ABSTRACT

Torquable tubular member for use in a flexible elongate device comprising an elongate tubular body having a cylindrical wall and a longitudinal axis extending longitudinally of the cylindrical wall. The cylindrical wall has formed therein a plurality of spaced-apart slots spaced longitudinally of the longitudinal axis. At least certain of the slots have a first portion which extends generally radially of the tubular body and a second portion which extends generally longitudinally of the tubular body.

18 Claims, 20 Drawing Sheets

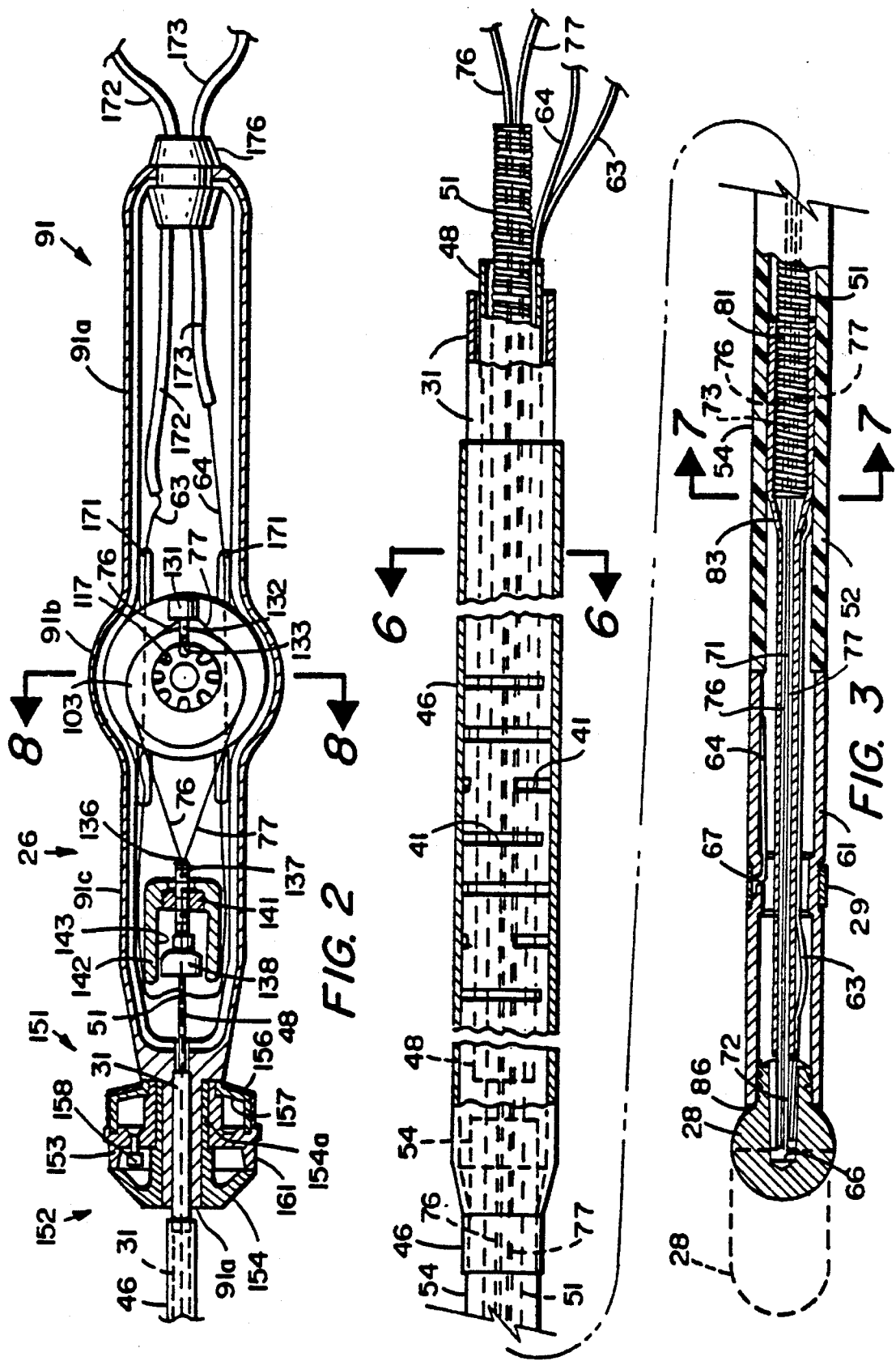

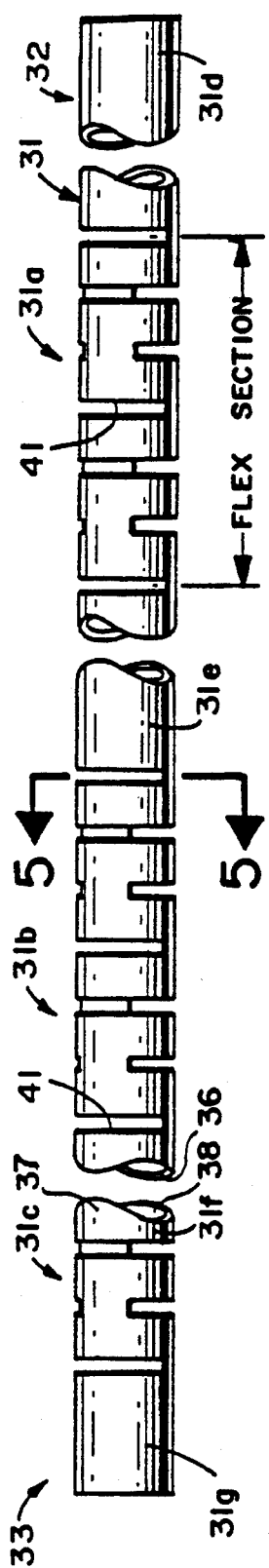
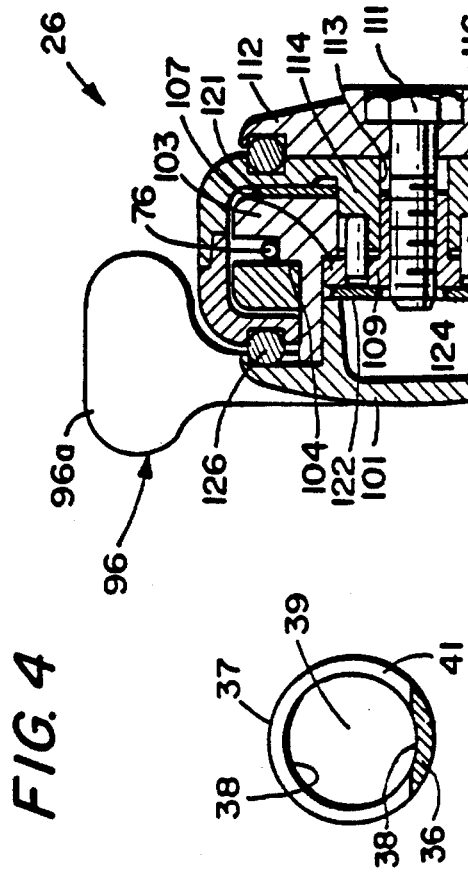
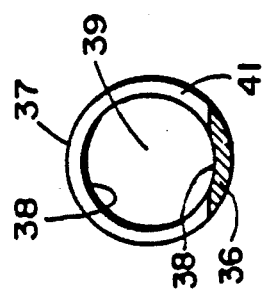
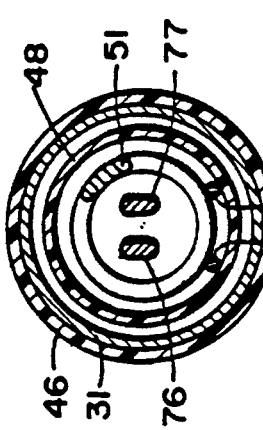
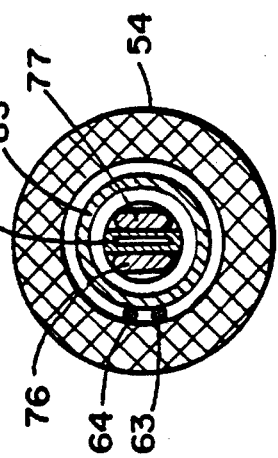

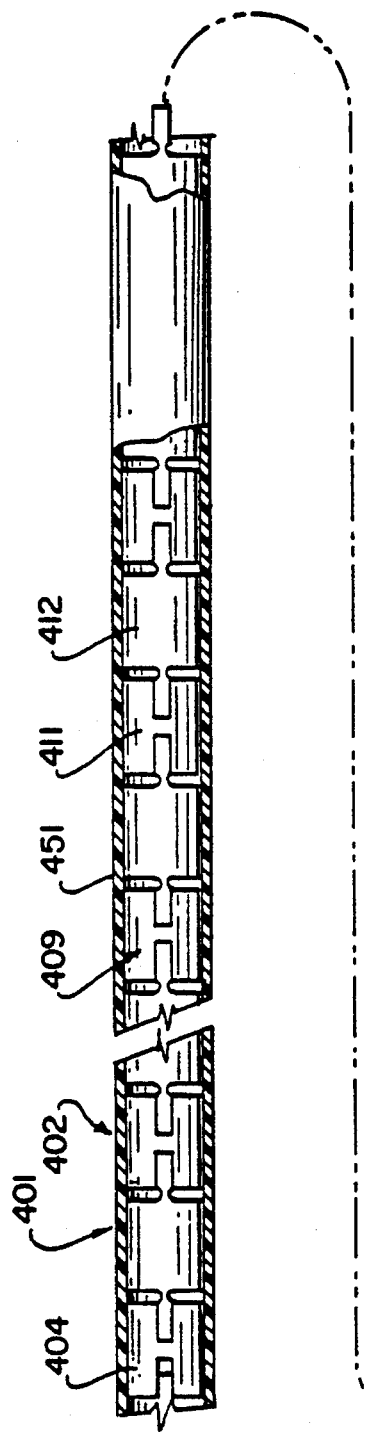
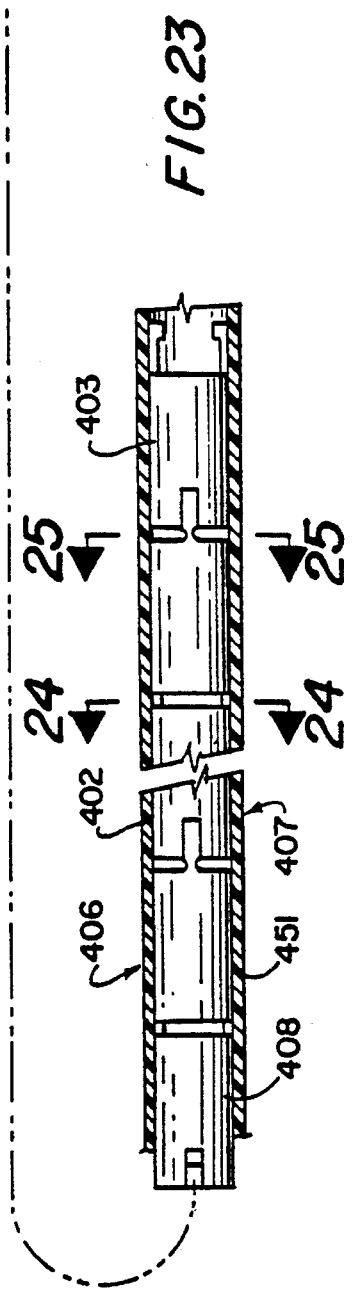
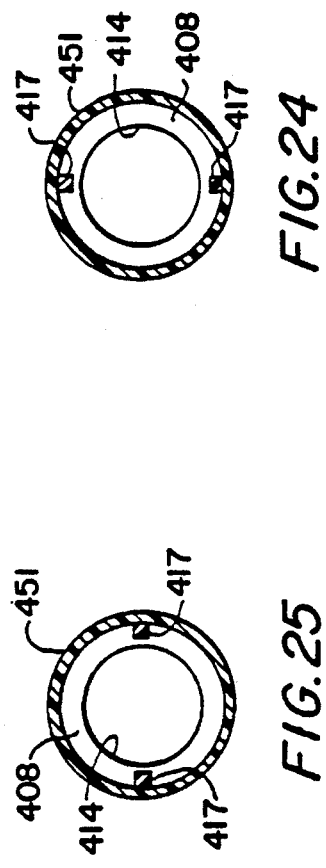
FIG.23
FIG.24
FIG.25

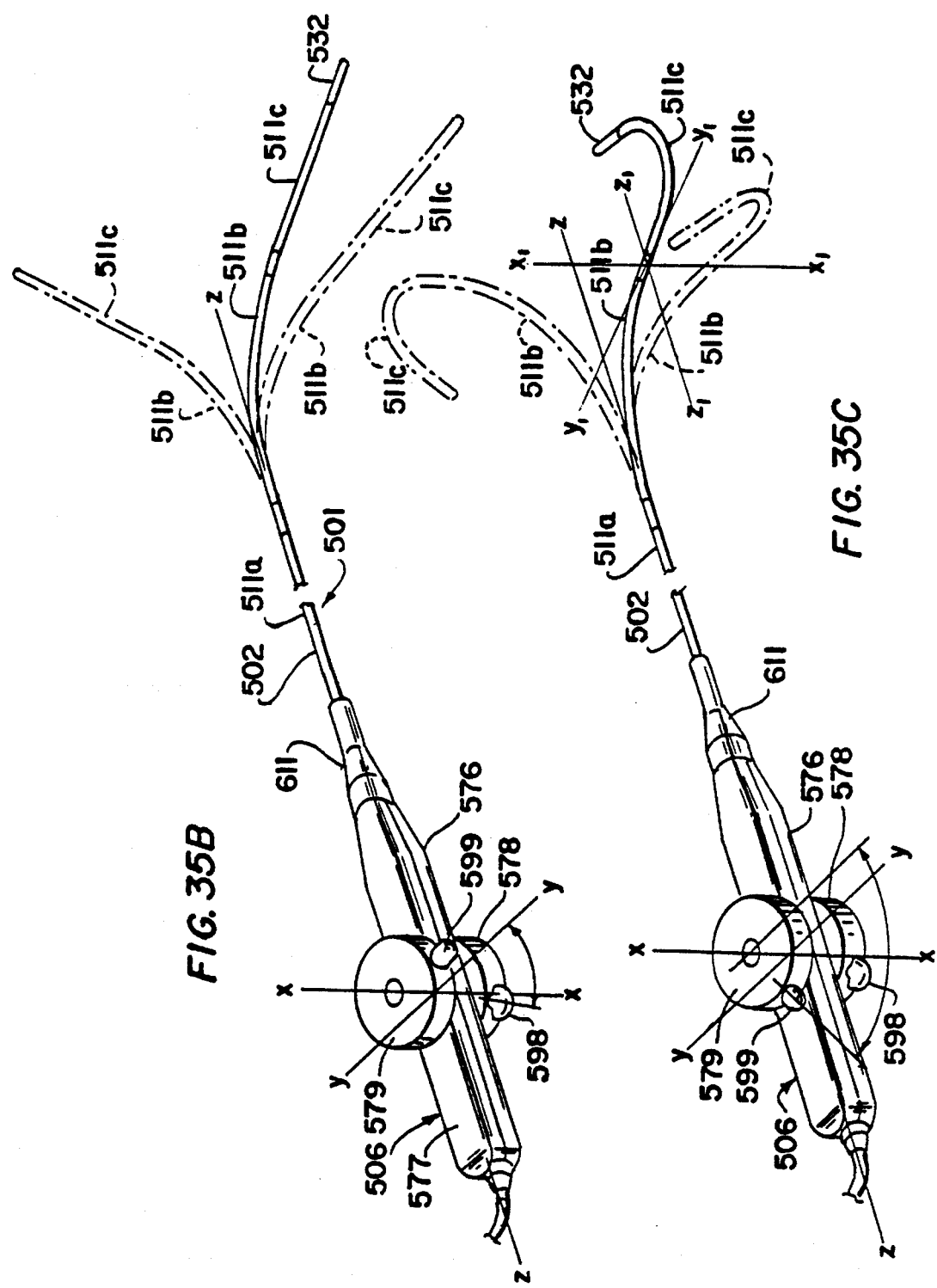

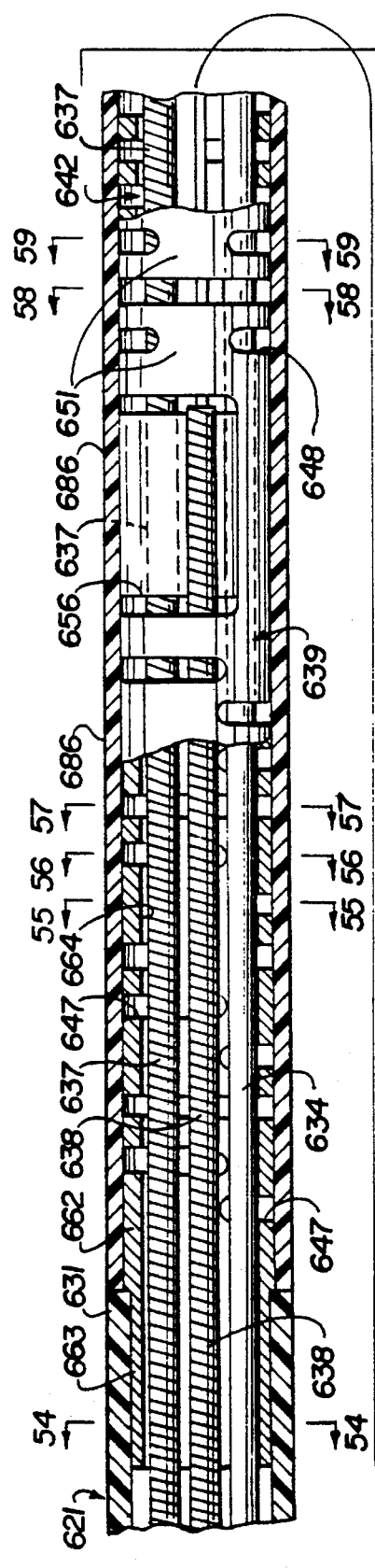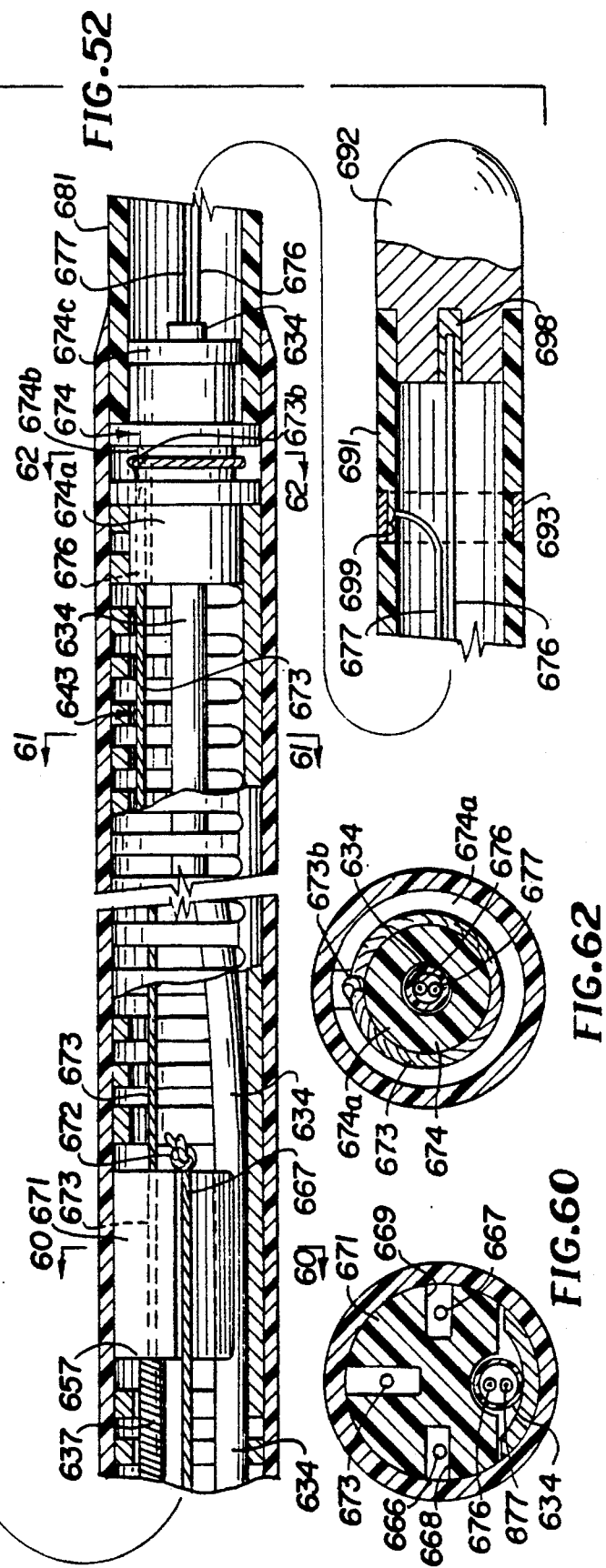

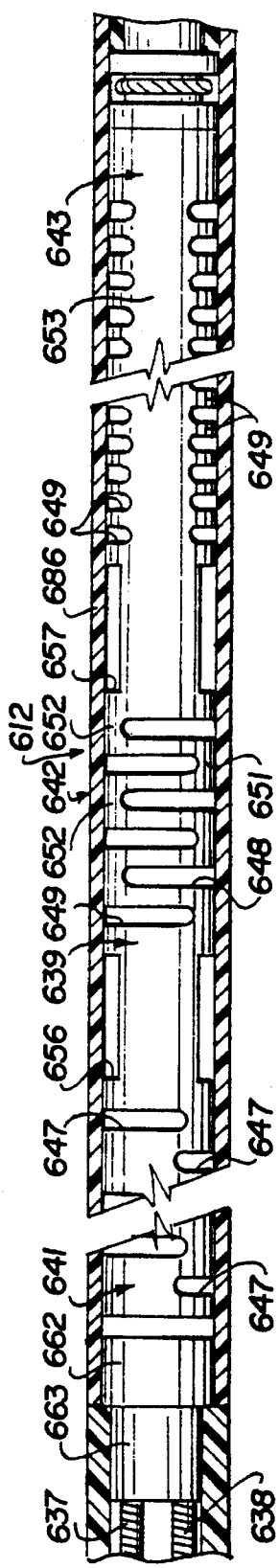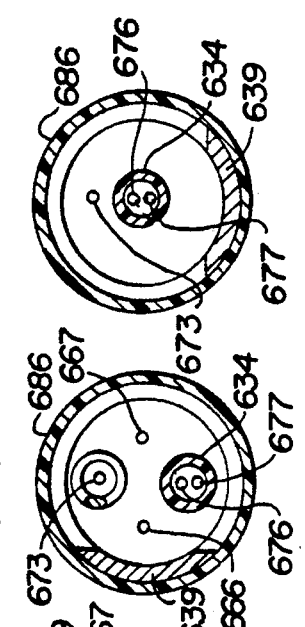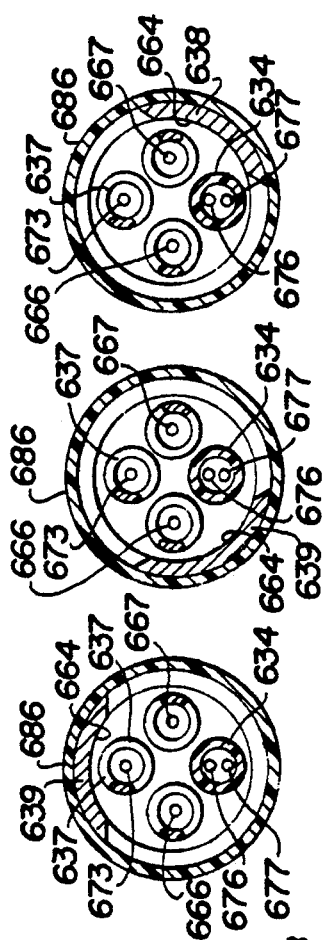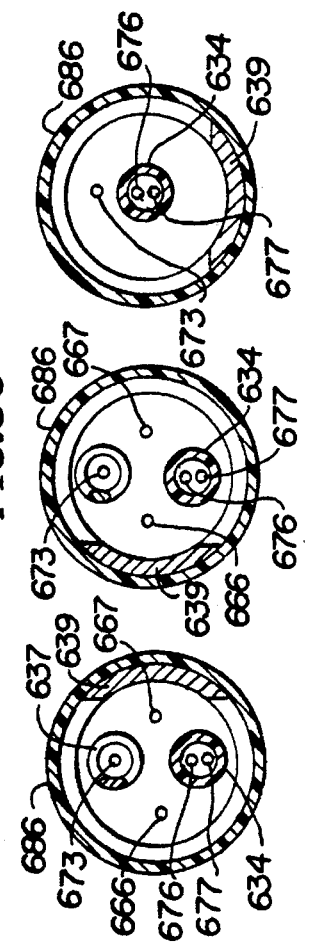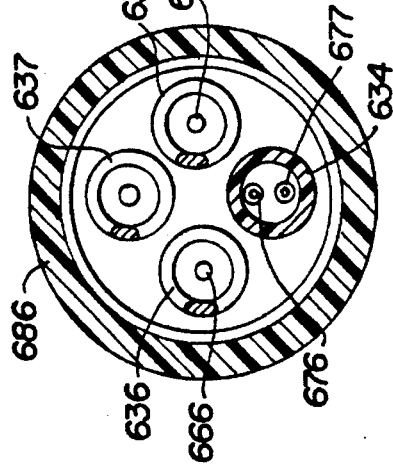

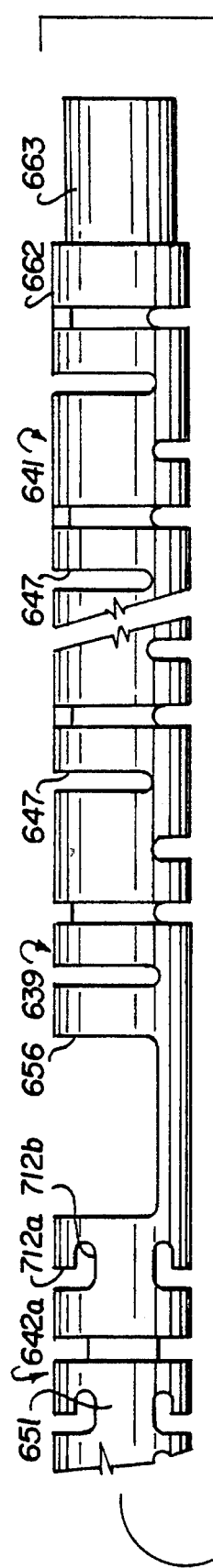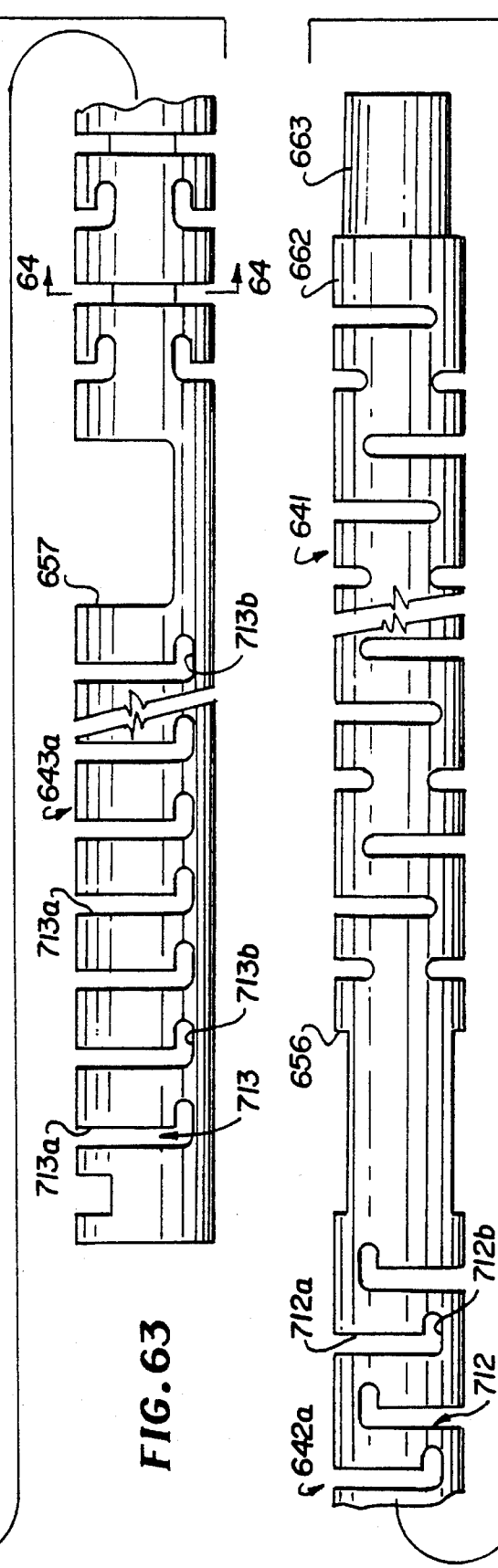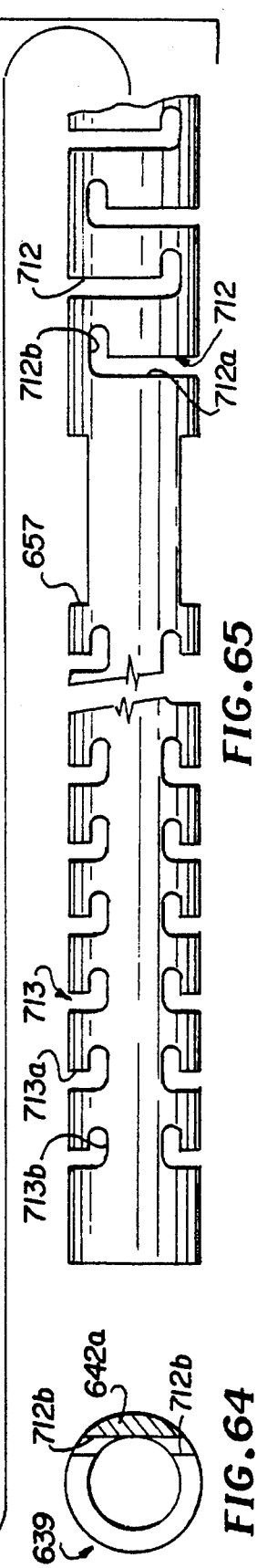
FIG. 63
FIG. 64
FIG. 65

TORQUABLE CATHETER AND TORQUABLE TUBULAR MEMBER FOR USE THEREWITH

This application is a division of application Ser. No. 08/126,681 filed Sep. 24, 1993, now U.S. Pat. No. 5,329,923, which is a continuation of Ser. No. 07/945,666 filed Sep. 16, 1992, abandoned, which is a continuation-in-part of Ser. No. 07/790,648 filed Nov. 8, 1991, abandoned, which is a continuation-in-part of Ser. No. 07/725,660 filed Jul. 3, 1991, abandoned, which is a continuation-in-part of Ser. No. 07/657,106 filed Feb. 15, 1991, abandoned.

This invention relates to a torquable catheter and a torque tube for use therewith.

In the past, steerable catheters have heretofore been provided to facilitate maneuvering in blood vessels. However, in the past with such devices it has been difficult to achieve a substantially one to one ratio of movement for the proximal and distal extremities of the catheter. There is therefore a need for a new and improved catheter which can achieve such a one-to-one ratio and torquable tubular member for use therewith.

In general, it is an object of the present invention to provide a torquable catheter in which a substantially one to one ratio of movement between proximal and distal extremities of the catheter can be achieved.

Another object of the invention is to provide a catheter of the above character which has the desired degree of flexibility.

Another object of the invention is to provide a catheter of the above character which can be utilized in a blood vessel.

Another object of the invention is to provide a catheter of the above character in which the distal extremity can be steered.

Another object of the invention to provide a torquable tubular member for use in the catheter of the above character which has improved flexibility.

Another object of the present invention is to provide a torquable tubular member of the above character in which the bending forces are distributed over a longer distance.

Another object of the invention is to provide a torquable tubular member of the above character in which different modes of bending can be achieved.

Another object of the invention is to provide a torquable tubular member of the above character which has greater flexibility.

Additional objects and features of the invention will appear from the following description of the particular embodiment as set forth in detail in conjunction with the accompanying drawings:

FIG. 2 is a plan view in cross-section of the steering handle of the catheter shown in FIG. 1.

FIG. 3 is a cross sectional view of the catheter shaft and distal extremity of the catheter shown in FIG. 1.

FIG. 4 is an elevational view of the torque tube utilized in the catheter shown in FIG. 1.

FIG. 5 is a cross-sectional view taken along the line 5—5 of FIG. 4.

FIG. 6 is a cross-sectional view taken along the line 6—6 of FIG. 3.

FIG. 7 is a cross sectional view taken along the line 7—7 of FIG. 3.

FIG. 8 is a cross sectional view taken along the line 8—8 of FIG. 2.

FIG. 23 is a plan view of still another embodiment of a torquable catheter incorporating the present invention.

FIG. 24 is a cross sectional view taken along the line 24—24 of FIG. 23.

FIG. 25 is a cross sectional view taken along the line 25—25 of FIG. 23.

FIG. 35B shows the manner in which the preform of the tractable portion formed in FIG. 35A can be further bent into a desired bend after the catheter has been introduced into the patient.

FIG. 35C is an isometric view similar to that shown in FIGS. 35A and 35B and showing the manner in which the distal extremity can be steered through a plane which corresponds to the plane of the handle for the catheter.

FIG. 52 is a enlarged view of the distal extremity of the torquable catheter shown in FIG. 51 partially in cross-section.

FIG. 53 is a view similar to FIG. 52, but at an angle rotated through 90°.

FIG. 54 is a cross-sectional view taken along the line 54—54 of FIG. 52.

FIG. 55 is a cross-sectional view taken along the line 55—55 of FIG. 52.

FIG. 56 is a cross-sectional view taken along the line 56—56 of FIG. 52.

FIG. 57 is a cross-sectional view taken along the line 57—57 of FIG. 52.

FIG. 58 is a cross-sectional view taken along the line 58—58 of FIG. 52.

FIG. 59 is a cross-sectional view taken along the line 59—59 of FIG. 52.

FIG. 60 is a cross-sectional view taken along the line 60—60 of FIG. 52.

FIG. 61 is a cross-sectional view taken along the line 61—61 of FIG. 52.

FIG. 62 is a cross-sectional view taken along the line 62—62 of FIG. 52.

FIG. 63 is a top plan view of another embodiment of a torquable tubular member for use in the torquable catheter shown in FIG. 51.

FIG. 64 is a cross-sectional view taken along the line 64—64 of FIG. 63.

FIG. 65 is a side elevational view rotated by 90° of the torquable tubular member shown in FIG. 63.

Figure 1:
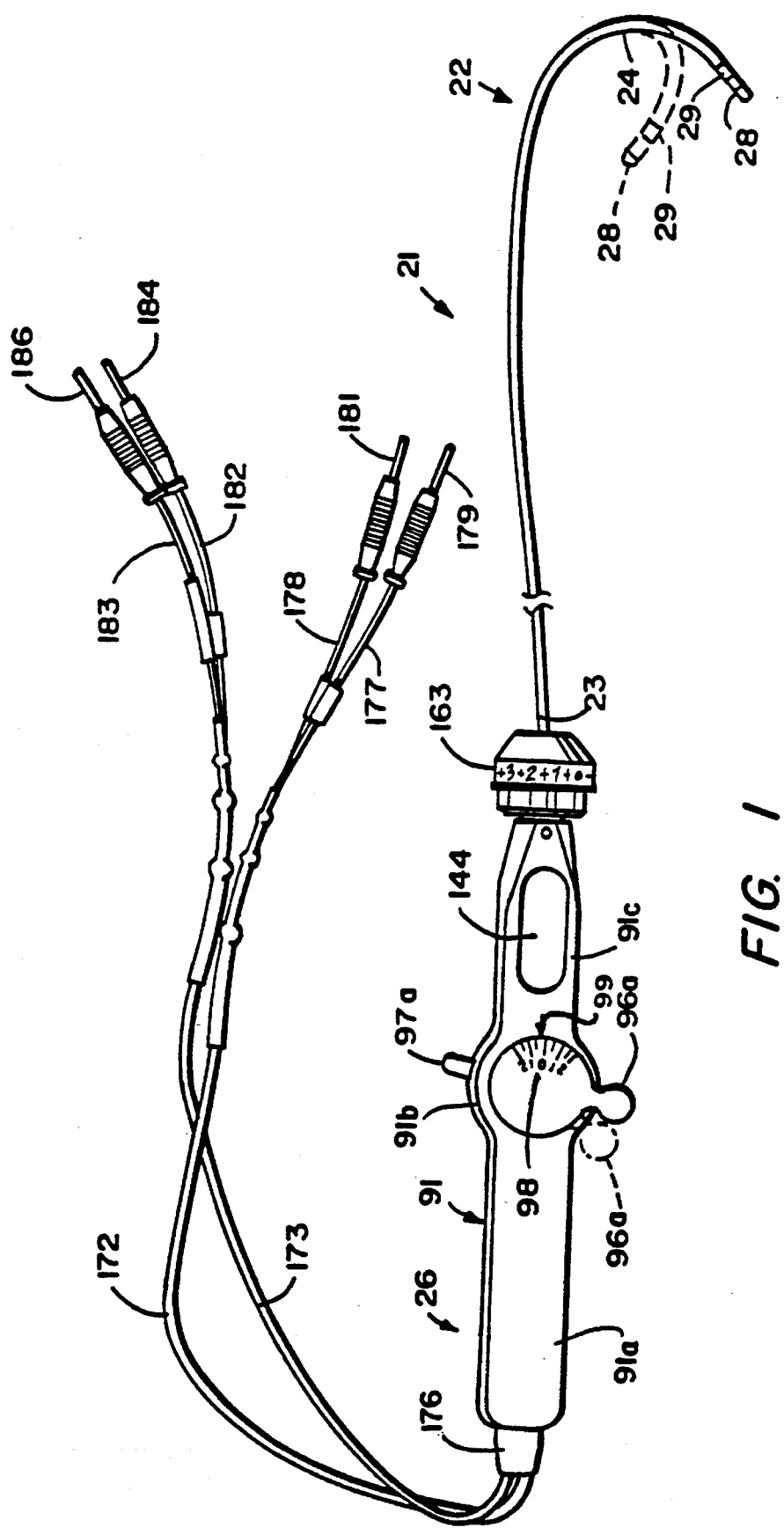
FIG. 1 is a plan view of a torquable catheter incorporating the present invention.

In general, the torquable catheter of the present invention is adapted to be inserted into and through a lumen of a blood vessel and comprises a flexible elongate tube or shaft having proximal and distal extremities and having a lumen extending therethrough. The shaft is comprised of a metal torquable tubular member extending for at least a portion of the length of the length of the shaft. The torquable tubular member has a cylindrical wall, with at least one flexible portion therein. The flexible portion is characterized in that a plurality of longitudinally spaced apart slots are provided in the cylindrical wall which extend through the wall with each of the slots subtending less then 360°. A flexible sleeve extends over the torquable tubular member and encases the torquable tubular member and permits flexing of the torque tube within the elastic limits of the torquable tubular member.

More particularly, as shown in FIGS. 1–8 of the drawings, the torquable catheter 21 incorporating the present invention consists of a flexible elongate tube or shaft 22 having proximal and distal extremities 23 and 24. A steering handle 26 is secured to the proximal extremity 23. At least one electrode, a first electrode 28 and preferably an additional or second electrode 29 are mounted on the distal extremity 24 in a manner hereinafter described.

The catheter shaft 22 consists of a flexible elongate torque tube or torquable tubular member 31 which extends at least over a portion of the catheter shaft 22 and as shown in FIG. 3 from the steering handle 26 to near the distal extremity 24 of the catheter shaft. The torque tube 31 is formed of a suitable material such as 13 gauge thin wall stainless steel. Such stainless steel tube 31 has an outer diameter of 0.095" and inside diameter of 0.077" to provide a wall thickness of 0.009". It should be appreciated that it is within the scope of this invention to utilize torque tubes of various diameters and wall thicknesses depending upon the torque capability required for the torque tube 31. For example, utilizing the same diameter, a different wall thickness ranging from 0.007" to 0.012" can be provided. The torque tube can have a suitable length as determined by the length of the catheter 21.

By way of example, a catheter constructed in accordance with the present invention had a torque tube 31 having a length of 38". A torque tube 31 having such a length is elongate and is flexible. However, to impart additional flexibility to the torque tube 31 while retaining its high torque capabilities, the torque tube 31 is provided with at least one flexible portion intermediate its ends and typically is provided with a plurality of such flexible portions. As shown in FIG. 4, three such flexible portions identified as 31a, 31b and 31c have been provided. These flexible portions 31a, 31b and 31c are spaced apart longitudinally of the torque tube 31 between the proximal and distal extremities 32 and 33 so that there remains solid portions 31d, 31e, 31f and 31g. The solid portion 31d can be characterized as a shaft portion, the portions 31e and 31f as intermediate portions and portion 31g as a tip portion. The torque tube 31 is formed by an elongate cylindrical wall 36 which has an outer cylindrical surface 37. It also has an inner cylindrical surface 38 which defines a lumen 39 which extends the length of the torque tube 31.

Each of the flexible portions 31a, 31b and 31c is comprised of at least one slot and preferably a plurality of slots 41 which extend through the cylindrical wall 36 and are spaced longitudinally of the torque tube 31. The slots 41 are radially offset with respect to each other. Each of the slots subtends less than one circumference of the tube wall 36 or in other words less than 360°. Preferably the slots subtend an angle ranging from 270° to 300°. Thus, as shown in FIG. 5, there is provided a slot 41 which is cut into the cylindrical wall until the inside surface 38 on the other side of the of the wall 36 is reached so that there remains material in the wall 36 which extends over 0.064" or approximately 60°. The slots 41 are radially offset with respect to each other by a suitable angle as for example 120°. However, these radial offsets can range from 30° to 120°. The slots 41 shown in the drawings extend transversely or normal to the longitudinal axis of the torque tube 31.

It should be appreciated, however, that if desired, the slots 41 can be formed at an angle from portions of a helix.

The distance between each slot 41 in a flexible portion can be defined as the pitch and can range from 0.03" to 0.09" and preferably approximately 0.055". A flexible length of the torque tube 31 can be considered to be a flexible portion associated with a solid wall portion as for example portions 31f and 31c.

The desired degree of flexibility in a flex portion can be varied by providing fewer or more slots 41 in a flex portion. Thus, there can be provided as few as a single slot to a total of 10 or more slots with the typical flex portion having seven slots as shown in the drawings. In order to give the flexibility of movement of a universal joint at least three slots offset by 120° increments should be provided. Alternatively, four slots offset in 45° can be provided to provide such motion flex portion will permit approximately 30° of bending on a ⅝" inside radius. Thus, two flex portions with no solid tubing in between would permit approximately 60° of bending on a ⅝" inside radius.

By way of example, a torque tube 31 having a length of 38" and made in accordance with the present invention had a tip portion 31g with has a length of ⅓". It had a first flex group comprised of five flex portions each having a length of 1" for a total of 5", a second flex group of seven flex lengths of 1½" each for a total of 10½" and a third flex group of 10 flex lengths of 2" each for a total of 20" and a shaft portion 31d having a length of 2". A flex length can be comprised of a single flex section plus a solid length of tubing ending at the first slot in the next flex section. By providing such flex groups, it has been found that the desired flexibility can be achieved for the catheter while still retaining high torque capabilities of the torque tube. It should be appreciated that additional flexibility can be obtained in the catheter by providing additional slots in the torque tube with some sacrifice in the torque capabilities of the torque tube.

A thin walled shrink tubing 46 made of a suitable material such as a polyolefin encapsulates the outer surface 37 of the torque tube 31. The tubing 46 is applied by slipping it over the outer surface 37 of the torque tube 31 and then heating the same to cause it to shrink tightly onto the torque tube 31 to be in direct contact therewith. The shrink tubing 46 serves several purposes. It serves to provide a protective wall for the catheter which encloses the torque tube 31 and provides a smooth outer surface with low friction to engage the wall of the vessel of the patient into which the catheter 21 is introduced. It also serves to prevent undue separation of the segments on the opposite sides of the slots 41.

The shrink tubing 46 is very flexible and permits desired flexing of the torque tube 31 but prevents undue bending or stress in the material of the side wall in any one slot and thereby prevents the placement of a permanent strain in any portion of the tube. In other words, the tubing 46 prevents bending or flexing of the torque tube beyond the point from which it will not yieldably return to its original configuration. The tubing 46 also serves to prevent blood or any other liquid in the lumen in which the catheter is introduced from entering into the slots 41 and causing possible clotting. The shrink tubing 46 can have an appropriate wall thickness such as 0.002" with a wall thickness ranging from 0.001 to 0.004".

A sleeve or tube 48 formed of a suitable insulating material such as a plastic as for example a polyimide is disposed within the torque tube 31 (see FIG. 5) which extends the length of the torque tube 31. An elongate tightly coiled coil spring 51 is disposed within the sleeve or tube 48 and also extends the length of the torque tube 41. The coil spring 51 is formed of a spring steel wire rectangular in cross section. It can have suitable inside and outside diameters, as for example an outside diameter of 0.0360" and an inside diameter of 0.0260" and a wall thickness of 0.005". The wire for the coil spring 51 can have side dimensions of 0.005" for a square cross section. The use of square wire for the coil 51 also serves to prevent collapsing of the turns of the coil during flexing of the catheter.

The distal extremity of the coil spring 51 extends beyond the distal extremity of the tube 31 and extends into a flexible braided tubular member 54 formed of a suitable material such as a plastic with braided wire embedded therein. The braided member 54 which extends within the shrink tubing 46 up to the distal extremity of the torque tube 31 to the line 56 shown in FIG. 3. The distal extremity of the insulating tube 48 extends to the line 57 in FIG. 3. The braided tubular member 54 extends distally beyond the distal extremity of the coil spring 51 and is bonded by a suitable means such as an adhesive (not shown) to a soft plastic tubing 61.

The tubing 61 carries the electrodes utilized in connection with the present catheter and as shown also serves to mount a first or tip electrode 28 and a second or ring electrode 29 hereinbefore described. Conductors 63 and 64 are connected to the electrodes 28 and 29. Conductor 63 extends into a recess 66 in the tip electrode 28 and conductor 64 extends through a hole 67 makes contact with the ring electrode 29.

Means is provided for causing bending of the distal extremity of the catheter and consists of a bendable flat spring element 71 which has a distal extremity 72 that is seated in the recess 66 provided in the tip electrode 28. The spring element also provided with a proximal extremity 73 seated in slots (not shown) in the distal extremity of the coil spring 51 so that the coil spring 51 serves as a substantially incompressible element in the catheter 21. First and second pull wires or elements 76 and 77 have their distal extremities bonded to opposite sides of the flat spring element 71. The pull wires or elements 76 and 77 extend into the proximal extremity of the catheter 21 by extending through the lumen 81 provided interiorly of the coil spring 51.

Additional shrink tube 83 is provided and extends from the distal extremity of the coil spring 51. The tube 83 surrounds the first and second pull wires 76 and 77 and the bendable spring element 71 and extends to the tip electrode 28. The recess or cavity 66 of the electrode 28 is filled with a suitable conducting material such as solder which serves to provide electrical contact to the leads 53 and also to hold the pull wires 76 and 77 and the bendable flat spring element 71 in place. An adhesive 86 can be provided in the space between the distal extremity of the tubing 61 and the outer surface of the tip electrode 28. The tip electrode 28 can have a suitable conformation such as spherical or elongate with a hemisphere tip, as shown.

The conductors or leads 63 and 64 for the electrodes 28 and 29 extend into the proximal extremity of the catheter 21 between the coil spring 51 and the braided tubular member 54 and thereafter between the coil spring 51 and the inner surface 38 of the torque tube 31.

As shown, the first and second pull wires 76 and 77 can be in the form of flat wires to minimize their space requirements. These first and second pull wires 76 and 77 can be identified as right and left pull wires extend to the proximal extremity of the catheter 21 through the torque tube 31 as do the conductors 63 and 64 into the steering handle 26.

The steering handle 26 consists of a housing 91 formed of a suitable material such as plastic. The housing 91 is formed of two mating parts 92 and 93 (see FIG. 8) which form two halves of the housing and which are fastened together by ultrasonic welding or an adhesive (see FIG. 1). This housing 91 has a handle portion 91a which is elongate and which is adapted to be engaged by the hand of the user. The housing is provided with a large cylindrical portion 91b which has a steering lever 96 and a locking lever 97 rotatably mounted thereon. The handles 96 and 97 are provided with enlarged finger engaging portions 96a and 97a respectively which extend slightly outward of the cylindrical portion 91b and extend inwardly diametrically of the housing as shown particularly in FIG. 8. The housing 91 is also provided with an elongate portion 91c which receives the proximal extremity of the shaft 22. Means is provided within the housing 91 for connecting the levers 96 and 97 to the pull wires 76 and 77 so that the pull wires can be pulled in accordance with the positioning of the steering lever 96 and locked in place by locking lever 97.

The steering lever 96 is secured to a circular cap 101 which has secured thereto a cylindrical skirt 102 of an eccentric 103. So that the eccentric 103 rotates with the cap 101 as the steering lever 96 is moved. The eccentric 103 is provided with an annular shoulder 104 which rides upon a washer 106 disposed within the part 92. The eccentric 103 is provided with another annular shoulder 107 that engages a shoulder 108 of a lock nut 109 which is threaded onto a cap screw 111. The cap screw 111 is mounted in a circular cap 112 mounted on the housing 91 on the opposite side of the cap 101 and has the locking lever 97 secured thereto. The lock nut 109 is slidably received within a bore 113 provided on a boss 114 formed on the part 93. Means is provided for preventing rotation of the lock nut 109 relative to the boss 114 and consists of a plurality of circumferentially spaced pins 116 that extend into the shoulder 108 of the nut 109 and into the boss 114 to thereby prevent rotation of the lock nut 109 but to permit movement longitudinally of the bore 113. A friction washer 121 is provided between the eccentric 103 and the interior of the housing 93. Another friction washer 122 is provided between the head 123 of the nut 109 and skirt 124 of the circular cap 101. O rings 126 and 127 are provided for forming seals between the circular caps 101 and 112 and the housing 91. The eccentric 103 is provided with an annular shoulder 128 which receives the pull wires 76 and 77. The steering lever 96 is provided with a scale 98 with a "0" indicating a center position and the numbers +1 to +5 indicating clockwise (and −1 to −5) indicating counterclockwise movement of the lever from the center position by approximately 45° in each direction from a marker 99 for a total of approximately 90°.

Means is provided for securing the proximal extremities of the pulling wires or elements 76 and 77 of the housing and consists of a holding block 131. The holding block 131 is rectangular in shape and is provided with a pin 132 which is seated within a recess 133. The pull wires 76 and 77 after they leave the eccentric 103 extend forwardly into a lumen 136 of a tension adjustment screw 137 which is provided therewith a slotted adjustment head 138. The adjustment screw 137 is threaded into a nut 139 and is disposed in a slot 141 provided in an H-shaped structure 142 (see FIG. 2) formed integral with the parts 92 and 93. The H-shaped structure 142 includes upstanding leg portions 142 which define a space 143 therebetween and permit adjustment longitudinally of the H-shaped structure 142. From FIG. 2, it can be seen that the coil spring 51 abuts the head 138 of the tension adjustment screw 137. A removable cover 144 is provided in the part 93 to permit access to the head 138 of the adjustment screw 137 to permit adjustment of the tension on the pull wires 76 and 77.

The proximal extremity of the torque tube 31 extends through a twist indicator assembly 151. The twist indicator assembly 151 consists of a housing 152 formed of a suitable material such as plastic. The housing is comprised of an rotatably adjustable intermediate part 153 which is formed of an opaque plastic and end parts 154 and 156. The end part 156 is formed of a transparent plastic and forms an annular bubble chamber 157 which can contain a suitable liquid such as a silicon fluid. A fill plug 158 is provided for filling the bubble chamber 157 and for introducing a small bubble therein in the chamber which can be visible through the transparent end part 156 which will serve to provide a vertical reference for the catheter as hereinafter described.

The intermediate part of 153 is provided with planar surface 161, which can carry indicia as for example, from 1–10 with a zero index indicated 162 and with numbers on one side +1, +2, ≠ on one side of zero and −1, −2, −3 on the other side of zero to give an indication as to the extent of rotation or twist of the catheter as hereinafter described. The other end part 154 provided with a truncated conical surface 166 and with a cylindrical skirt 167 which fictionally engages the torque tube 31 so that the housing 152 rotates with the torque tube.

The conductors 63 and 64 extend through the steering handle 26 as shown particularly in FIG. 2 and are disposed beneath the eccentric 103 and in grooves 171 provided in the housing 91 and are connected to cables 172 and 173 (see FIG. 1) which extend through a strain relief fitting 176 mounted in the housing 91 of the steering handle 26. The cable 172 terminates in two conductors 177 and 178 which are connected to terminals 179 and 181 (see FIG. 1). Similarly, the cable 173 terminates in two conductors 182 and 183 which are provided with terminals 184 and 186. The terminals 179 and 181 and 184 and 186 are adapted to be plugged into electronic equipment of a conventional type to provide mapping and/or ablation capabilities as well as diagnostic and pacing capabilities for a catheter of the present invention.

Operation and use of the catheter having high torque capacity shown in FIGS. 1–8 and method for utilizing the same may now briefly be described as follows. Let it be assumed that it is desired to carry out mapping in a chamber of the heart as for example the right ventricle and thereafter if necessary to carry out an ablation procedure. The catheter can be advanced into the chamber of the heart in a conventional manner as for example, through a femoral artery. The catheter can be advanced into a femoral artery by use of a guiding catheter. The physician while holding the steering handle 26 in one hand introduces the distal extremity of the catheter 21 into the vessel of the patient having a lumen therein. The catheter has sufficient rigidity so that it can be pushed or advanced into the lumen while observing the advancement under a fluoroscope. In view of the fact that the catheter is relatively flexible and small in size, as for example ⅛" or less, it can be readily advanced through the arterial vessel of the patient into a chamber of the heart.

After it has been determined that the distal extremity of the catheter 21 is in the desired chamber of the heart and the electrodes 28 and 29 are positioned therein, mapping procedures can thereafter be carried out. Typically, a mapping procedure is carried out by bringing the electrodes 28 and 29 into contact with the wall defining a chamber of the heart. As soon as they have been brought into contact with the wall, a potential measurement can be made. The positioning of the distal extremity of the catheter so that the electrodes are brought into contact with the wall forming the chamber is carried out by utilizing the first and second or right and left pull wires or elements 76 and 71 to cause bending of the distal extremity of the catheter in a desired direction. This can be accomplished by operating the steering lever 96 to cause bending of the tip in the desired direction. When the desired position is reached, the pull wires 76 and 77 can be locked into position by rotation of the locking lever 97 to fictionally engage the eccentric 103 and hold it in the desired position until the mapping measurement has been completed.

Progressive incremental mapping of the interior of the chamber of the heart can be accomplished by incrementally rotating the distal extremity of the catheter. This is readily accomplished with a catheter of the present invention which has high torque capabilities to make it possible to achieve a one-to-one torquing movement for the distal extremity of the catheter as the steering handle 26 is rotated by the holding hand of the physician. Thus, for example, if it is desired to rotate the distal extremity of the catheter 21 by a suitable incremental rotational movement as for example 5%, this can be accomplished by rotating the steering handle 26 by that amount. The electrodes can then be brought into contact with the wall of the chamber by use of the pull wires 76 and 77 to bend the distal extremity of the catheter by operation of the steering lever 96 by a finger of the holding hand. Another incremental potential measurement can be made. Additional incremental rotation of the distal extremity of the catheter 21 can then be accomplished and thereafter using the pull wires 76 and 77 to achieve appropriate contact with the wall forming the chamber of the heart. Another potential measurement can then be made. In this way the entire circumferential surface defining the chamber can be mapped.

The twist indicator 151 which has been provided makes it possible for the physician to keep track of the rotation which he has imparted to the distal extremity of the catheter from a reference position. The bubble in the bubble chamber provides a vertical reference for the scale or indicia 163 appearing on the annular surface 161 of the twist indicator assembly 151. The physician when he believes he has the catheter in a good position which he wishes to use as a reference rotatably adjusts the intermediate part so that the "0" on the scale 161 is in registration with the bubble in the bubble chamber 157. By observing the bubble and the scale 161, the physician is able to keep track of where the catheter is with respect to the "0" reference position previously set. This makes it possible for the physician to know precisely where in a rotational aspect the distal extremity of the catheter 21 is positioned.

The torque tube 31 within the catheter 21 provides possible to provide very high torque capabilities for the catheter giving a one-to-one torque transmission from the steering handle 26 to the distal extremity of the catheter 21. The construction of the handle is such so that the catheter 21 can be operated with one hand of the physician while the other hand can grasp the handle portion 91a of the steering handle 26 while permitting the fingers of the same hand to operate the steering lever 96 as well as the locking lever 97.

The tension adjustment screw 111 is readily adjusted to achieve the desired tension on the pull wires 76 and 77 so that the pull wires 76 and 77 are immediately responsive to the positioning of the steering lever 96 and will cause bending of the distal extremity of the catheter 21 in relatively smooth curves in opposite directions. By observing the scale 98 on the steering lever 96 with respect to the marker 99, the amount of bending and the direction of the bending of the distal extremity of the catheter can be ascertained. By way of example at a certain predetermined scab setting, a J bend is placed in the distal extremity of the catheter 21. The physician by knowing those scale settings can obtain predetermined bends by moving the steering lever 96 to scale settings.

The use of the slotted torque tube 31 makes it possible to achieve the desired degree of flexibility within the catheter while still retaining high torque capability of the catheter so that a one to one relationship between movement of the steering handle and the distal extremity of the tip of the catheter can achieved. These high torque capabilities can be achieved without significantly reducing the longitudinal rigidity of the catheter.

Another embodiment of a torquable catheter incorporating the present invention is shown in FIGS. 9 through 16. As shown therein, the torquable catheter 201 consists of a flexible elongate tube or shaft 202 which has proximal and distal extremities 203 and 204. The steering handle 206 is substantially identical to the steering handle 26 hereinbefore described, and is secured to the proximal extremity 203 of the tube or shaft 202. At least one electrode and preferably first and second electrodes are provided in which the first electrode is in the form of a ring electrode 207 and the second electrode is in the form of a tip electrode 208.

Figure 9:
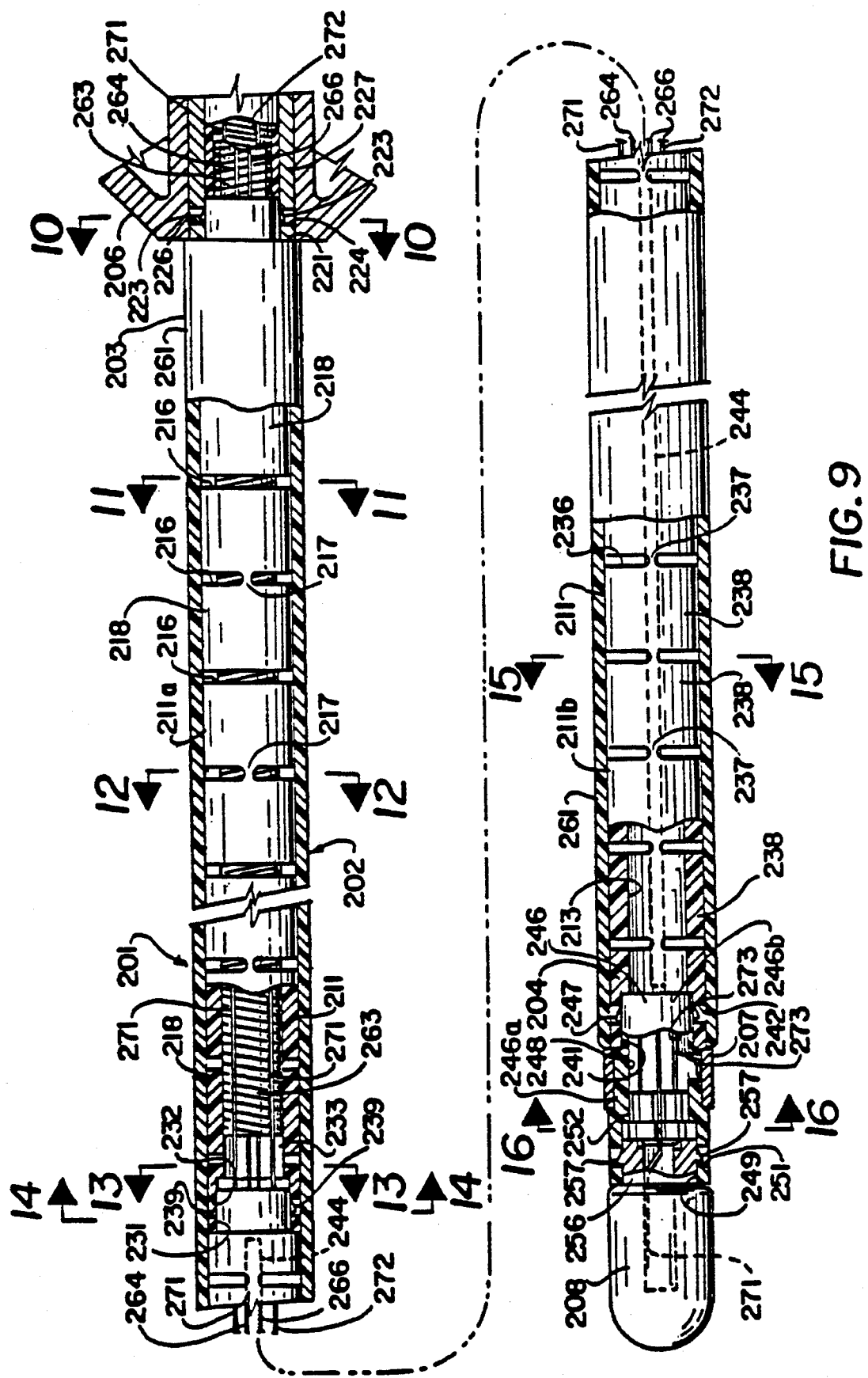
FIG. 9 is a plan view of another embodiment of a torquable catheter incorporating the present invention.

The catheter tube or shaft 202 consists of a flexible elongate torque tube 211 which extends for at least a portion of the length of the catheter shaft 202 and as shown in FIG. 9 extends from the steering handle 206 to near the distal extremity 204. In the present embodiment of the torquable catheter 201, the torque tube 211 is formed of (TINEL®), an alloy of nickel and titanium manufactured and sold by Raychem Corporation, 300 Constitution Drive, Menlo Park, Calif. 94025. TINEL has been selected for use in the torque tube 211 because of its superelastic characteristics which provides the desired flexibility, kink resistance, torquability and shape recovery. This "TINEL" material can be provided in tubular form as shown in FIG. 4 with slots 41 formed therein in the same manner as hereinbefore described. However, because of the superelastic characteristics of the "TINEL", it has been found that a different type of joint construction can be utilized because of the capability of "TINEL" to withstand repeated bending and that much more severe bends can be accommodated without breaking.

The torque tube 211 can have the same dimensions as hereinbefore previously described, as for example it can be in the form of 13-gauge, thin-wall hypodermic tubing having an outside diameter of 0.095", a wall thickness of 0.009" and an inside diameter of 0.077" to form a bore 213. As also pointed out previously, torque tubes of various diameters and wall thicknesses can be provided depending upon the particular application as hereinbefore previously pointed out. The torque tube 211 has a suitable length as determined by the length of the torquable catheter 201.

Figure 11:
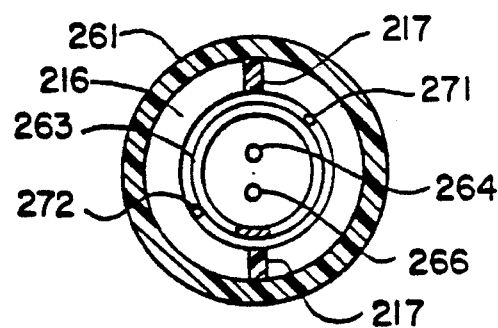
FIG. 11 is a cross sectional view taken along the line 11—11 of FIG. 9.
Figure 12:
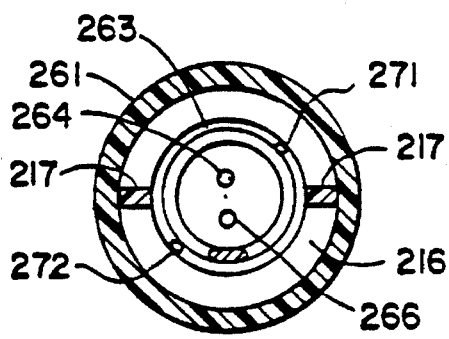
FIG. 12 is a cross sectional view taken along the line 12—12 of FIG. 9.

In connection with the present invention, it has been found desirable to provide the torque tube 211 in two sections, one section 211a having a length ranging from 2 to 3 feet which provides 4-way or universal joint action, and a second section 211b having a suitable length as for example 2–3 inches which provides 2-way bending. Although the torque tube 211 is flexible and can be bent, additional flexibility is provided in both of the sections 211a and 211b as hereinafter described. In section 211a, opposed semicircular slots 216 are formed in spaced apart positions spaced axially of the section 211a. The slots 216 extend through the wall of the torque tube 211 a sufficient distance so that there remain circumferentially spaced apart hinges 217 which serve to join adjacent parts 218 forming the section 211. As shown, the hinges 217 are spaced 180° apart and can have a suitable thickness as for example 0.006". The slots 216 can have a suitable width as for example 0.012". Every other pair of opposed slots 216 are offset 90° with respect to the adjacent slots as shown in FIG. 9 and by the cross sectional views as shown in FIGS. 11 and 12. The slots 216 can be formed in a suitable manner as for example by a spark erosion technique identified as EDM machining.

By offsetting the pairs of slots 216 in this manner, it is possible to achieve 4-way bending of the torque tube which is very similar to a universal joint action. By way of example, utilizing the dimensions set forth above, it has been found that a 180° bend can be achieved in less than 2 inches of the torque tube section 211a. It should be readily appreciated that the amount of bending is determined by the spacing between the pairs of opposed slots 216 and also the width of the slots, with the width of the slot determining the amount of bending which can occur between any two adjacent parts of the section 211a.

By providing two hinges 217 between adjacent parts 218 there is increased capability of transferring torque from one part to the other over the embodiment which is shown in FIG. 4 in which only a single portion 41 remains to transfer torque from one adjacent part to another. By utilizing the superelastic "TINEL" as the material for the torque tube 211, the hinges 217 are also superelastic and provide the capability for repeated hinging without danger of breaking.

Figure 10:
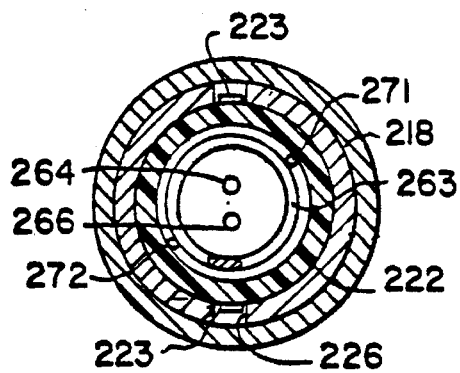
FIG. 10 is a cross sectional view taken along the line 10—10 of FIG. 9.

As shown in FIG. 10, the proximal extremity of the section 211a of the torque tube 211 is provided with an annular recess 221 to provide a cylindrical portion 222 of reduced diameter which has formed thereon a pair of teats 223 spaced 180° apart having lips 224 which are adapted to seat in bores 226 spaced 180° apart and extending at right angles to the axis of the torque tube 211 in the cylindrical member 227 which corresponds to the portion 91a of the handle 26 as shown in FIG. 2. In this way it can be seen that the section 211a of the torque tube 211 can be snapped into position in engagement with the handle by the lips 224 of the teats 223 being seated within the bores 226.

Figure 13:
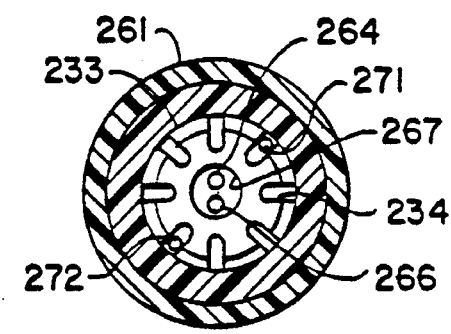
FIG. 13 is a cross sectional view taken along the line 13—13 of FIG. 9.
Figure 14:
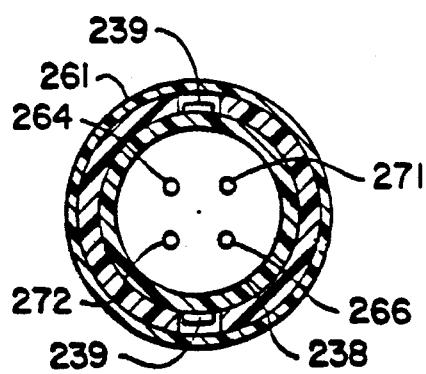
FIG. 14 is a cross sectional view taken along the line 14—14 of FIG. 9.

The distal extremity of the section 211a is provided within a large cylindrical recess 231 which opens forwardly. A pair of diametrically opposed bores 232 are provided in the distal-most part 218 of the section 211a and extend perpendicular to the axis of the section 211a and open into the cylindrical recess 231. A flanged insert 233 has its flange disposed within the cylindrical recess 231 with the remaining portion thereof extending into the adjacent part 218. A plurality of circumferentially spaced-apart slots 234 are provided in the insert 233 and extend in a direction parallel to the axis of the flanged insert 233. By way of example as shown in FIG. 13, eight of such slots 234 can be provided which are equally spaced apart around the circumference of the flanged insert 233. The slots 234 are used for purposes hereinafter described.

The torque tube section 211b is formed in a manner similar to that utilized for section 211a, the principal differences being that alternate opposed sets of slots are not offset by 90° because it is only desired to achieve 2-way bending by the relatively short tip section 211b. Thus, there are provided pairs of opposed slots 236 having a suitable width as for example 0.012" spaced apart a suitable distance as for example 0.110". The slots 236 are cut to a sufficient depth so that there remain a pair of hinges 237 spaced 180° apart which form connections between adjacent parts 238 of the section 211b. It can be seen that the hinges 237 lie in a single plane so as to permit bending in only two directions, forward and back with respect to the hinges 237. The hinges again have a suitable width as for example 0.006". The most proximal part 238 of the section 211b is provided with an annular recess 237 to provide a cylindrical portion 238 in which there are provided a pair of teats 239 spaced 180° apart having the same shape as the teats 223. These teats 239 engage the bores 232 in the section 211a.

Figure 15:
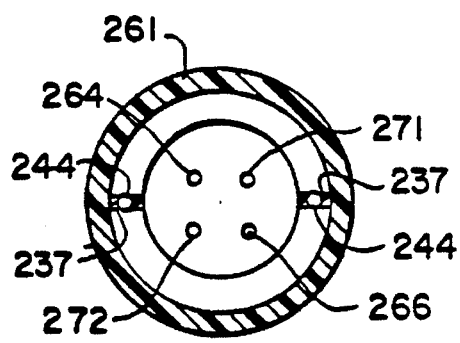
FIG. 15 is a cross sectional view taken along the line 15—15 of FIG. 9.
Figure 16:
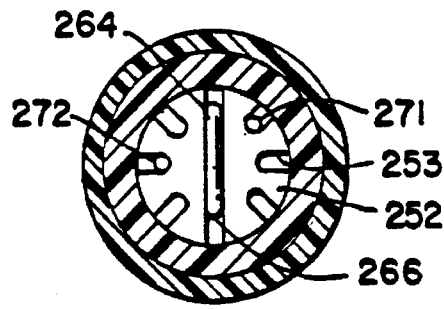
FIG. 16 is a cross sectional view taken along the line 16—16 of FIG. 9.

In order to provide a return memory at the distal extremity of the torque tube 211, "TINEL" superelastic wire 244 by Raychem Corporation, 300 Constitution Drive, Menlo Park, Calif. 94025, is utilized having a diameter ranging from 0.008" to 0.012" and preferably a diameter of 0.010" which extends longitudinally of the section 211b through the hinges 237 as shown particularly in FIG. 15. This superelastic wire, because it provides extreme flexibility, is kink resistant and provides shape recovery to the distal extremity of the torquable catheter when the distal extremity is permitted to return to its original condition.

The most distal part of the section 211b is provided with a large cylindrical recess 241. A pair of bores 242 spaced 180° apart extend into the recess 241 at right angles to the axis of the recess. A ring electrode retainer 246 is mounted within the recess 241. The retainer 246 is provided with cylindrical portions 246a and 246b of reduced diameter. The ring electrode 207 is mounted on the portion 246. A pair of teats 247 are spaced 180° apart and are provided on the portion 246b and are seated within the bores 242. A retainer 246 is provided with a bore 248 which is of the same size and is in registration with the bore 213 of the sections 211a and 211b. An enlarged cylindrical recess 249 is provided in the retainer 246. A pair of oppositely disposed bores 251 are provided in the retainer 246 and open into the cylindrical recess 249 at right angles to the axis of the recess. A flanged insert 252 similar to the flanged insert 233 hereinbefore described is disposed within the cylindrical recess 249 and is provided with circumferentially spaced slots 253. The tip electrode 208 is formed of a suitable material such as platinum and is formed as a cylinder which is provided with a hemispherical distal surface. The tip electrode 208 is mounted upon cylindrical tip electrode mounting 256 in a suitable manner such as by soldering. The mounting 256 is provided with a pair of teats 257 spaced 180° apart which are seated within the bores 251 of the retainer 246.

The flanged inserts 233 and 252, as well as the retainer 246 and the top electrode mounting 256, can be formed of a suitable material such as plastic.

A protective cover 261 formed of shrink tubing similar to the shrink tubing 46 hereinbefore described is provided. This shrink tubing is formed of polyolefin and encapsulates the outer surface of the torque tube 211 and extends from the ring electrode 207 at the distal extremity to the proximal extremity adjacent the steering handle 206. As pointed out previously, the protective cover 261 serves to prevent blood and other body fluids from entering into the slotted torque tube 211 while still permitting the desired bending of the torque tube. It also provides a smooth outer surface with low friction to facilitate movement of the torquable catheter tool in a vessel. As pointed out previously, the protective cover 261 can have a suitable wall thickness ranging from 0.001" to 0.004" and preferably 0.002".

An elongate, tightly coiled coil spring 263 is provided within the torque tube 211 and extends from the insert 233 to within the proximal extremity of the handle 206 as shown in FIG. 9. It can be sized so it fits within the torque tube 211 and, as pointed out previously, can be of square cross section to obtain the tight coiling to prevent collapsing of the turns of the coil on each other during flexing and compression of the coil spring.

First and second or right and left pull wires 264 and 266 are provided within the coil spring 263 and are connected to handle 206 in the same manner that the pull wires in the previous embodiments are connected to the handle 26. The pull wires 264 and 266 extend from the handle 206 through the coil spring 263 and thence through the central bore 267 provided in the insert 233 and then through the section 211b of the torque tube 211 and through two of the recesses 253 provided in the insert 252. The distal extremities of the pull wires 264 and 266 are then bent over the distal extremity of the insert 252 and are secured thereto by suitable means such as an adhesive.

The pull wires 264 and 266 can be formed of a suitable material such as "TINEL" superelastic wire supplied by Raychem Corporation, 300 Constitution Drive, Menlo Park, Calif. 94025. The use of such a material for the pull wires 264 and 266 is desirable because of its good flexibility, its kink resistance, and its shape recovery which facilitates returning the distal extremity of the torquable catheter 201 to its normally relatively straight condition from a bent position into which it is formed by operation of the handle 206 on the pull wires 264 and 266.

First and second insulated conductors 271 and 272 extend from the handle 206 and into the section 211a of the torque tube 211 between the interior of the torque tube section 211a and the exterior of the coil spring 263 and then through two of the recesses 234 of the insert 233 as shown in FIG. 13, and then through the torque tube section 211b through the retainer 246 through slot 253 in the insert 252 and then into the mounting 256 where it is connected to the tip electrode 208 by suitable means, such as soldering. The insulated connector 272 extends through a slot 273 provided in the retainer 246 and is secured to the ring electrode 207 by suitable means such as soldering.

The operation and use of the torquable catheter 201 as shown in FIGS. 9 through 16 and the method for utilizing the same is very similar to that hereinbefore described with respect to the previous embodiments. However, it should be appreciated that the torquable catheter tool which is provided with the "TINEL" torque tube provides extreme flexibility making it possible to bend the distal extremity of the catheter about a relatively sharp curve by operation of the handle 206 in either of two directions in a single plane. With rotation of the torquable catheter 201 by turning or rotation of the handle 206 it is possible to position the distal extremity of the torquable catheter 201 in any desired position within a chamber of the heart. The use of the TINEL pull wires 264 and 266 aids in returning the distal extremity of the catheter into its normal position. The use of the "TINEL" hinges interconnecting the parts provides excellent torque transmission characteristics between the parts while at the same time permitting repeated bending of the torquable catheter without danger of the hinges breaking or failing.

Still another embodiment of a torquable catheter 301 incorporating the present invention is shown in FIGS. 17 through 22. The torquable catheter 301 consists of the flexible elongate tube or shaft 302 having proximal and distal extremities 303 and 304. The proximal extremity is connected to a steering handle 306 of the type hereinbefore described. The catheter shaft 302 consists of a flexible elongate torque tube 307 which extends for at least a portion of the catheter shaft 302 which is formed of a plastic. A plastic suitable for this purpose is polypropylene which, in addition to being very strong, provides a desired hinge action which may be flexed repeatedly, as for example millions of times, without breaking.

The torque tube 307 is formed in two sections 307a and 307b, in which section 307a permits 4-way bending whereas section 307b permits 2-way bending as described in connection with a previous embodiment of the torquable catheter. The section 307a has a length of 2–3 feet and section 307b has a length of 2–4 inches. Section 307a is provided with pairs of opposed semicircular slots 308 which extend through the wall of the plastic torque tube 307 a sufficient distance so that there remains a pair of hinges 309 which are spaced 180° apart having a suitable width as for example 0.006" and with the slots having a width of suitable dimension as for example 0.012". The pairs of opposed slots 308 are spaced apart by a suitable distance as for example 0.100" with every other pair of slots being offset by 90° so that the hinges 309 lie in two planes which are angularly offset with respect to each by 90° to provide the 4-way bending similar to that obtained by universal joint hereinbefore described. The hinges 309 provided bending between adjacent parts 311 to permit flexing of the hinges between the parts in an amount determined by the width of the slots 308.

The section 307a can be formed of one or more units 312 as for example units having a length of 4 to 6 inches which are fitted together as hereinafter described to provide the 4-way section 307a of a suitable length as for example 2 to 3 feet. The unit 312 can be provided with mating proximal and distal extremities in which a cylindrical portion 313 of reduced diameter is provided having oppositely disposed teats spaced 180° apart being provided thereon. The distal extremity is provided with an enlarged cylindrical recess 316 which is sized to fit the cylindrical portion or extension 313 of reduced diameter and is provided with bores 317 spaced 180° apart and opening into the recess 316 at right angles thereto. The bores 317 are adapted to receive the teats 314 making it possible to secure the units to each other in a linear fashion to provide a 4-way bendable section 307a of a desired length. A pair of interiorly disposed slots 318 are provided within each of the units 312 and are spaced 180° apart and open into a central bore 319 which extends through each of the units 312 for receiving first and second pull wires 321 and 322. An elongate coil spring 324 of the type hereinbefore described is provided within the section 307a and extends the length of the same as hereinafter described.

The two-way bendable section 307b is provided with opposed semi-circular slots 326 which extend substantially through the wall of the tubular section 307b so that there remains a pair of hinges 327 spaced 180° apart. The slots 326 have a suitable width as for example 0.012" and are spaced apart a suitable distance as for example 0.100" to provide hinges 327 between parts 328 which lie on a plane so as to permit flexing in two directions. The proximal extremity of the section 307b is connected to the distal extremity of the section 307a by a cylindrical spring backup module 331 which is provided with a cylindrical extension 332 having teats 333 provided 180° apart thereon which engage the bores 317 in the distal extremity of the section 307a. As can be seen, the distal extremity of the spring 324 abuts against the cylindrical extension 332. The other end of the spring backup module 331 is provided with a cylindrical recess 334 having diametrically extending bores 336 extending into the recess. The proximal extremity of the section 307b is provided with a cylindrical extension 337 having teats 338 mounted thereon spaced 180° apart which are received by the bores 336 to secure the section 307b to the section 307a.

In a similar manner, the distal extremity of the section 307b is provided with a cylindrical recess 341 having diametrically extending bores 342 opening therein. The recess 341 is adapted to have mounted therein a cylindrical steering wire retainer 346 which is provided with a cylindrical extension 347 having a pair of teats 348 mounted 180° apart thereon which are adapted to seat in the bores 342. The pull wires 321 and 322, which also can be called steering wires, extend through the section 307a between the interior of the section 307a and the exterior of the coil spring 324 through the spring backup module 331 and then through the section 307b disposed in elongate recesses 349 provided therein on opposite sides of a central open bore 351 which extends through the section 307b. The pull wires 321 and 322 can be formed of a suitable material such as "KEVLAR". The distal extremities of the pull wires 321 and 322 extend into the steering wire retainer 346 and are secured therein by a retaining ring 352 which is secured to the retainer by suitable means such as an adhesive. The retaining ring 352 is provided with a central bore 353 which is in axial alignment with the bore 351 of the section 307b.

If desired, a soft tip 356 formed of a suitable material such as a latex can be removably secured to the distal extremity of the retainer 346.

The bore 351 in the section 307 is in axial alignment with the bore 361 provided in the spring backup module 331 and with the central bore provided in the spring 324.

Figure 17:
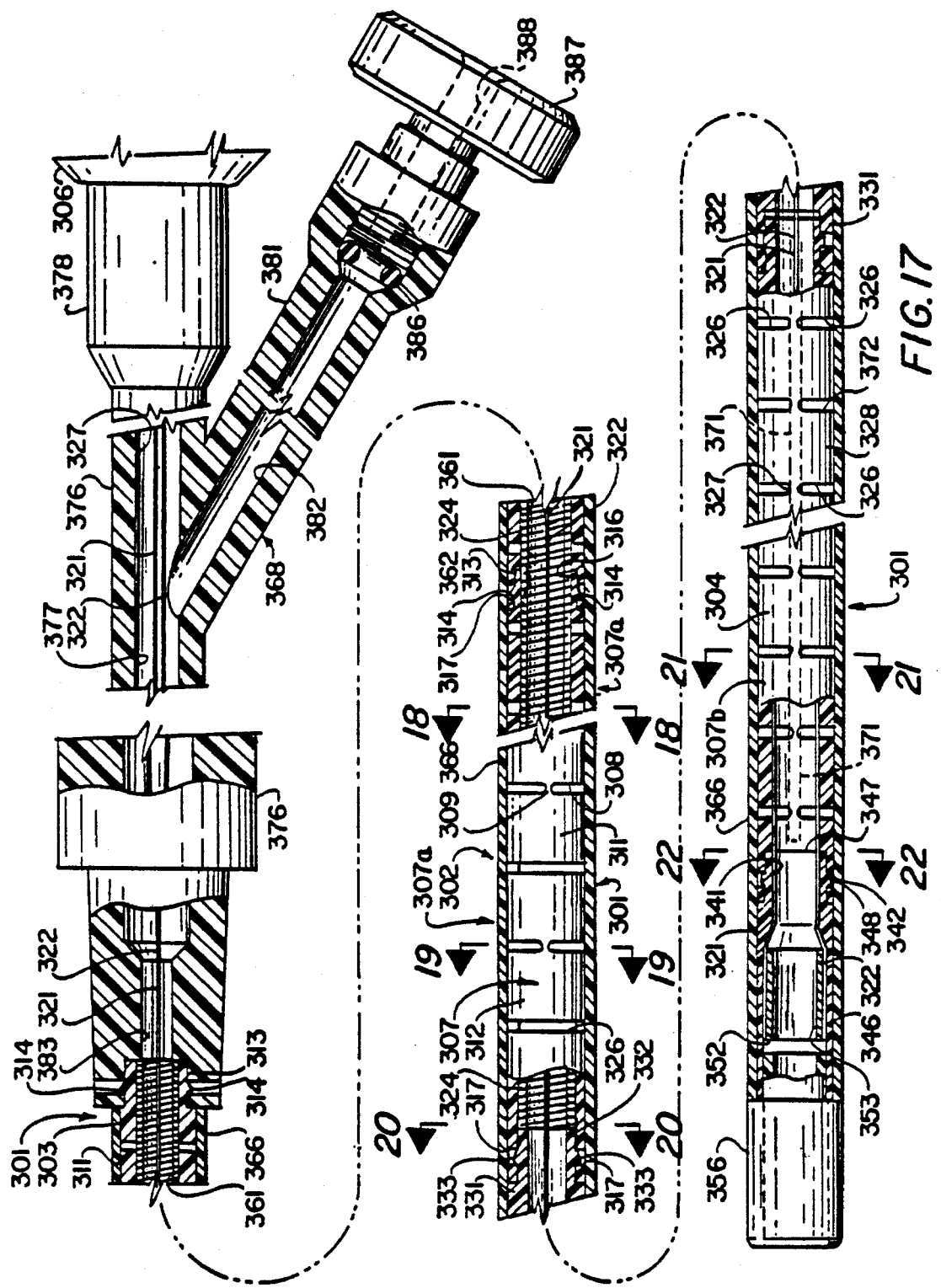
FIG. 17 is a plan view of still another embodiment of a torquable catheter incorporating the present invention.
Figure 18:
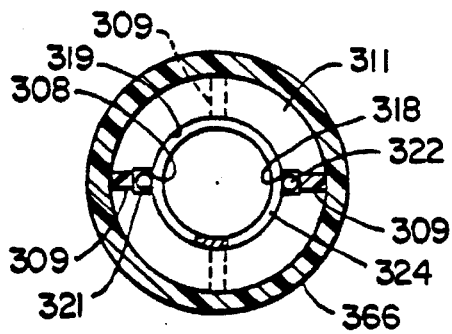
FIG. 18 is a cross sectional view taken along the line 18—18 of FIG. 17.
Figure 19:
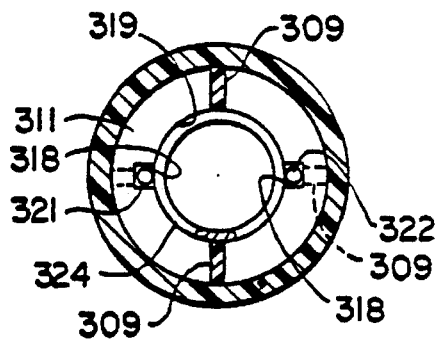
FIG. 19 is a cross sectional view taken along the line 19—19 of FIG. 17.
Figure 20:
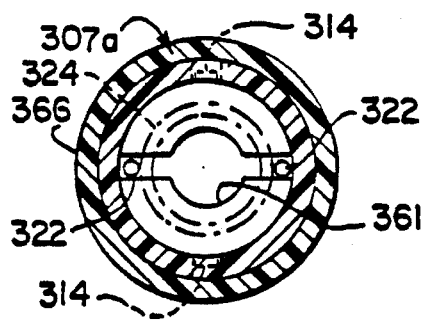
FIG. 20 is a cross sectional view taken along the line 20—20 of FIG. 17.
Figure 21:
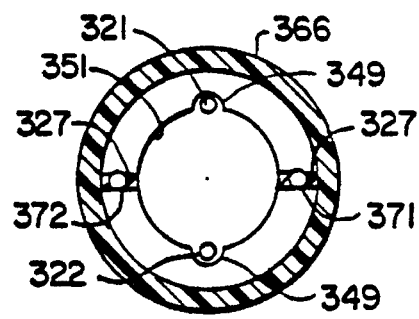
FIG. 21 is a cross sectional view taken along the line 21—21 of FIG. 17.
Figure 22:
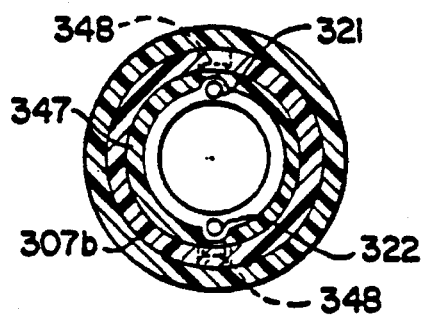
FIG. 22 is a cross sectional view taken along the line 22—22 of FIG. 17.
Figure 26:
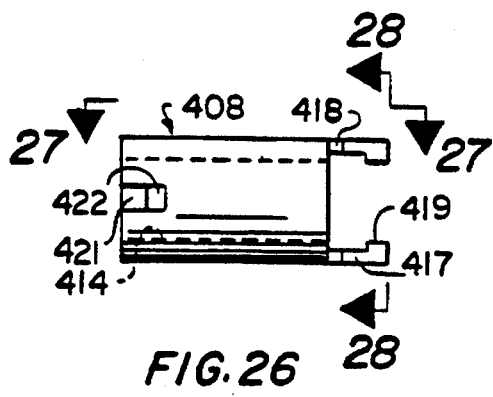
FIG. 26 is a side elevational view of a module A utilized in the catheter shown in FIG. 23.
Figure 28:
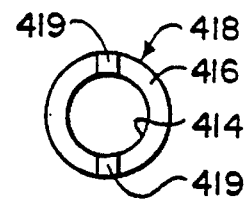
FIG. 28 is an end view of the module shown in FIG. 27 looking along the line 28—28 of FIG. 26.
Figure 27:
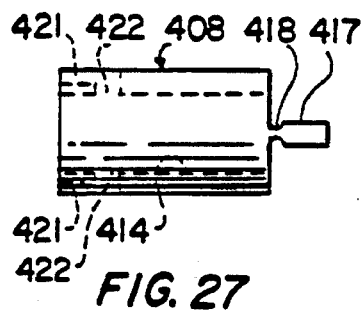
FIG. 27 is a view of a module looking along the line 27—27 of FIG. 26.
Figure 29:
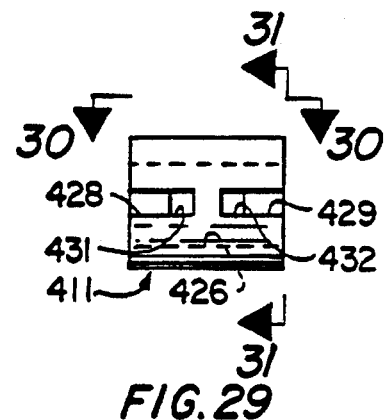
FIG. 29 is a side elevational view of another module utilized in the catheter shown in FIG. 23.
Figure 30:
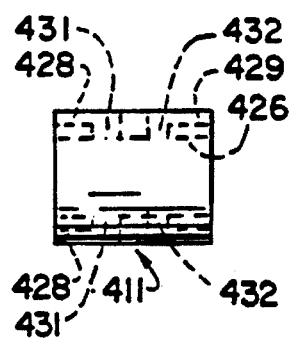
FIG. 30 is a view of the module shown in FIG. 29 looking along the line 30—30 of FIG. 29.
Figure 33:
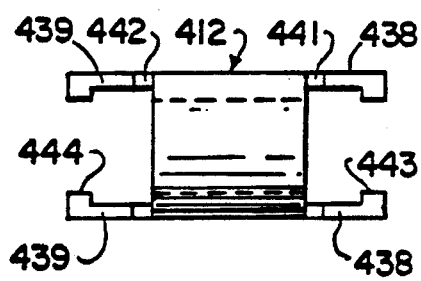
FIG. 33 is another view of the module shown in FIG. 32 looking along the line 33—33 of FIG. 32.
Figure 32:
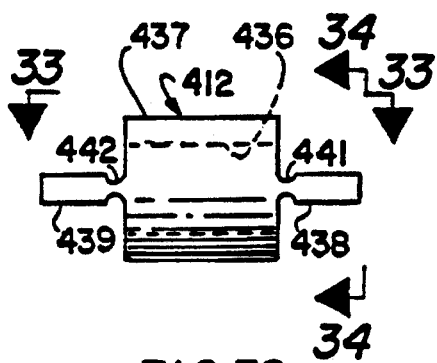
FIG. 32 is a side elevational view of another module utilized in the catheter as shown in FIG. 23.
Figure 31:
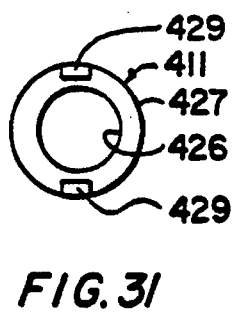
FIG. 31 is an end elevational view of the module shown in FIG. 29 looking along the line 31—31.
Figure 34:
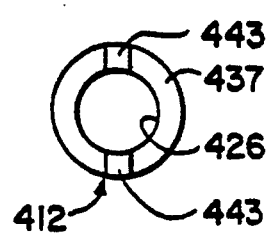
FIG. 34 is an end view of the module shown in FIG. 32 looking along the line 34—34 of FIG. 32.

A protective cover 366 formed of a suitable material such as polyolefin shrink tubing is provided for the exterior of the torque tube 307 and extends from the distal extremity of the catheter from the retainer 346 over the sections 307b and 307a up to a eye adapter 368 into which the torque tube section 307a extends with the coil spring 324 therein as shown in FIG. 17.

In order to provide shape recovery to the distal extremity of the torquable catheter 301, a pair of superelastic wires formed of a suitable material such as "TINEL" of a suitable size such as 0.010" in diameter are provided in the section 307b of the torque tube 307. As shown particularly in FIG. 21, these wires 371 and 372 are insert-molded into the hinges 327 of the section 307b and extend longitudinally through the length thereof. These superelastic insert-molded wires 371 and 372 urge the distal extremity 304 to its normally straight condition after it has been formed into a bend by the steering handle 306 and then released.

The wye adapter 368 is provided with a central leg or arm 376 which has a central bore 377 therein through which the pull wires 321 and 322 extend. The central arm is provided with a fitting 378 which is adapted to be secured to the handle 306 in the manner hereinbefore described with respect to the previous embodiments of the torquable catheter. The pull wires 321 and 322 are connected into the handle in the same manner and are operated in the same manner to provide the desired bending of the distal extremity of the catheter 301.

The wye adapter 368 is also provided with a side arm 381 which is provided with a central bore 382 that is in communication with a bore 383 which is in communication with the bore 361 extending through the coil spring 324. The side arm 381 is also provided with an O-ring 386 and a thumbscrew 387 which is threaded therein, and is adapted to clamp the O-ring 386 about any device (not shown) which extends through a bore 388 provided in the thumbscrew 387 through the O-ring 386 and into the bores 382 and 383. Such a device can extend into the bore 361 of the coil spring 324 and through the bores 351 and 353 provided in the distal extremity of the catheter and out through the open end. Thus, by way of example in connection with the present invention, it is possible to readily provide a open central lumen access having a diameter of 0.052" through the 2-way flex section 307b and a 0.038" diameter central lumen access through the 4-way flex section 307a. It can be readily be seen that this central lumen is a size that can accept many different types of medical devices for conducting operations in the human body.

The operation and use of the torquable catheter 301 is very similar to that hereinbefore described with the exception that rather than being utilized for mapping and ablation, the present torquable catheter can be utilized in conjunction with other devices for performing various types of operations in the human body. The distal extremity of the torquable catheter can be bent into any desired conformation by the steering handle 306 by operations on the pull wires 321 and 322. When the pull wires 321 and 322 are released, the distal extremity of the catheter will be urged to return to its normal relatively straight condition by the superelastic "TINEL" wires 371 and 372. The use of the wye adapter 368 permits insertion of medical devices into the body without loss of blood or other fluids by use of the thumbscrew 387 clamping the O-ring 386 about the device after it has been positioned within the human body.

Still another embodiment of a torquable catheter 401 incorporating the present invention is shown in FIGS. 23 through 34. As shown therein, it consists of a shaft 402 which is provided with proximal and distal extremities 403 and 404. The shaft 402 consists of a flexible elongate torque tube 406 which extends for at least a portion of the shaft 402. The torque tube 406 consists of a 4-way bend section 407 which is comprised of a plurality of axially aligned joined-together modules 408 and the 2-way bend section 409 which is comprised of axially aligned joined-together modules 411 and 412.

The modules 408, 411 and 412 are formed of a suitable material such as an injection moldable plastic material such as polypropylene which is capable of providing living hinges as hereinafter described.

The module 408 is in the form of a cylinder and has a suitable dimension such as an outside diameter of 0.095" and a cylindrical bore 414 extending longitudinally thereof and having a diameter of a suitable dimension as for example 0.060" to provide a cylindrical wall 416 having a thickness of 0.0175". The module 408 can have a suitable length as for example 0.188". A pair of longitudinally extending tangs or legs 417 are provided which are formed integral with the wall 416 and are disposed parallel to the longitudinal axis of the bore 414. The legs 417 can have a suitable length as for example 0.042" and have a width of 0.018" and a thickness of 0.010". The legs 417 are provided with portions which have a reduced cross section in a direction perpendicular to the longitudinal axis of the bore 414 and serve to form "living hinges" to permit repeated flexing without breaking of the legs with respect to the wall 416 as hereinafter described. Ears 419 are formed integral with the outer extremities of the legs 417 and are generally rectangular in cross section and can have a suitable thickness as for example 0.018" and a length of 0.018" inches. The hinges 418 are formed by providing radii of a suitable size as for example 0.006" in a hinge having a length of 0.012". A pair of recesses 421 are provided in the outer surface of the wall 416 on the end opposite the legs 417 spaced 180° apart which are offset 90° with respect to the legs 417 of another module 408. The recesses 421 are sized so that they can receive the legs 417 of another module 408 and have a width of approximately 0.018" and a length of 0.030". The recesses 421 extend into rectangular recesses or holes 422 which extend through the wall 416. These holes or recesses 422 are dimensioned to receive the ears 419 and thus are provided with sides having a dimension of 0.018".

It can be seen that the holes or recesses 422 are positioned in such a manner so that when the modules 408 are assembled as shown in FIG. 23 with the legs 417 extending into the recesses 421 and with the ears 419 seated within the holes or recesses 422, there is provided a spacing between the axially aligned, joined modules 408 of a suitable dimension as for example 0.012" corresponding to the length of the hinges 418 so as to permit bending of the modules 408 with respect to each other in a 4-way motion which is similar to the universal joint action hereinbefore described. As can be seen, bending of one module with respect to the other in a pair of modules 408 can occur in two directions at right angles to the hinges 418 whereas another pair of modules can be bent in two different directions offset by 180° with respect to the directions in which the modules in the first-named pair can be bent. The modules 411 forming a part of the 2-way bend section 409 are also of cylindrical form and can have an outside dimension as for example 0.095" and a length of 0.114" with a cylindrical bore 426 having a suitable diameter as for example 0.060" to provide a wall 427 having a thickness of 0.0175". Pairs of recesses 428 and 429 spaced 180° apart are provided on opposite ends of the cylindrical wall 427 and extend through the outer surface thereof and are in axial alignment with each other and extend longitudinally of the bore 426. The recesses 428 and 429 open respectively into rectangular recesses or holes 431 and 432 provided in the wall 427. These recesses 428 and 429 and the holes or recesses 431 and 432 are dimensioned in a manner similar to the recesses 421 and the holes or recesses 422 in the module 408.

The module 412 is also cylindrical in shape and is provided with an outside diameter of 0.095" with a cylindrical bore 436 extending longitudinally therethrough and having a diameter of 0.060" and a wall 437 having a thickness of 0.0175". Pairs of legs 438 and 439 are formed integral with the wall on opposite ends of the wall 437 and extend outwardly therefrom. The legs in each pair spaced 180° apart are in axial alignment with the legs of the other pair. The legs can have suitable dimensions as for example a length of 0.060" and a width of 0.018". Hinges 441 and 442 are formed by providing portions of reduced cross sectional area and width of the legs by providing hinges having a length of 0.012" and by forming radiuses of 0.006". Rectangular ears 443 and 444 are provided on the outward extremities of the legs 438 and 439 and have suitable dimensions as for example 0.018" by 0.018". The ears 443 and 444 and the legs 438 and 439 are dimensioned so that they can fit within the recesses 428 and 429 and 431 and 432 provided in the module 411.

As can be seen in FIG. 23, the modules 411 and 412 are joined together by snapping the legs 438 and 439 into the recesses 428 and 429 so that the ears 443 and 444 snap into the recesses 431 and 432 to provide the 2-way bend section 409 so that the hinges 441 and 442 are axially aligned and to provide a suitable spacing between the modules as for example 0.12" to permit 2-way bending of this section of the shaft.

A cover 451 of shrink tubing is provided on the exterior of the assembled modules 408, 411 and 412. This cover 451 ensures that the modules 408, 411 and 412 will remain joined together by preventing the tangs or legs with their ears formed integral therewith from disengaging the corresponding recesses or popping apart. The shrink tubing also prevents the bending of the modules with respect to each other within the limits of the spacing provided between the modules and the hinges joining the modules. The shrink tubing cover 451 also serves to prevent blood from entering into the lumen of the catheter formed by the respective bores provided in the modules. The shrink tubing made of a suitable material such as polyolefin permits easy flexing and bending of the shaft 402 of the catheter 401.

When utilized in the catheter as for example of the type hereinbefore described, the 4-way bend section 407 can have a suitable length as for example 2–3 feet whereas the 2-way bend section 409 can have a suitable length as for example 2–3 inches. In this way it is possible to provide a catheter a which is very flexible and in which the bending in the distal extremity is limited to 2-way bending to facilitate positioning of the distal extremity while at the same time providing excellent torque transmission from the proximal to the distal extremity of the shaft 402.

The modular type construction which is shown in FIG. 23 lends itself to use in various types of torquable catheters. As in the previous embodiments, the proximal extremity can be connected to a steering handle (not shown) of the type hereinbefore described in which the pair of pull wires (not shown) can extend through the central lumen. In addition, it should be appreciated that if desired the 4-way bend section can be provided with a coil spring disposed interiorally of the lumen as described in the previous embodiments. If electrodes are to be carried by the distal extremity of the catheter, the conductive wires connected thereto also can extend through the lumen and then through the steering handle in the manner hereinbefore described. Also it should be appreciated that since a large central lumen has been provided in the catheter, other types of medical type devices can be inserted through this lumen for performing operations at the distal extremity of the catheter.

A still further embodiment of a torquable catheter 501 incorporating the present invention is shown in FIGS. 35 through 50. The torquable catheter 501 consists of a flexible elongate shaft 502 which has a proximal extremity 503 and a distal extremity 504. A handle 506 is secured to the proximal extremity 503.

The flexible elongate shaft 502 can have a suitable length as for example 45 inches. It consists of a torque tube 511 which extends for at least a portion of the length of the shaft 502. The torque tube 511 is provided in three sections or portions in which portion or section 511a is the main torque tube section and portion or section 511b is the tractable or curved portion of the torque tube and portion or section 511c is the tip section or portion of the torque tube 511.

Figure 36:
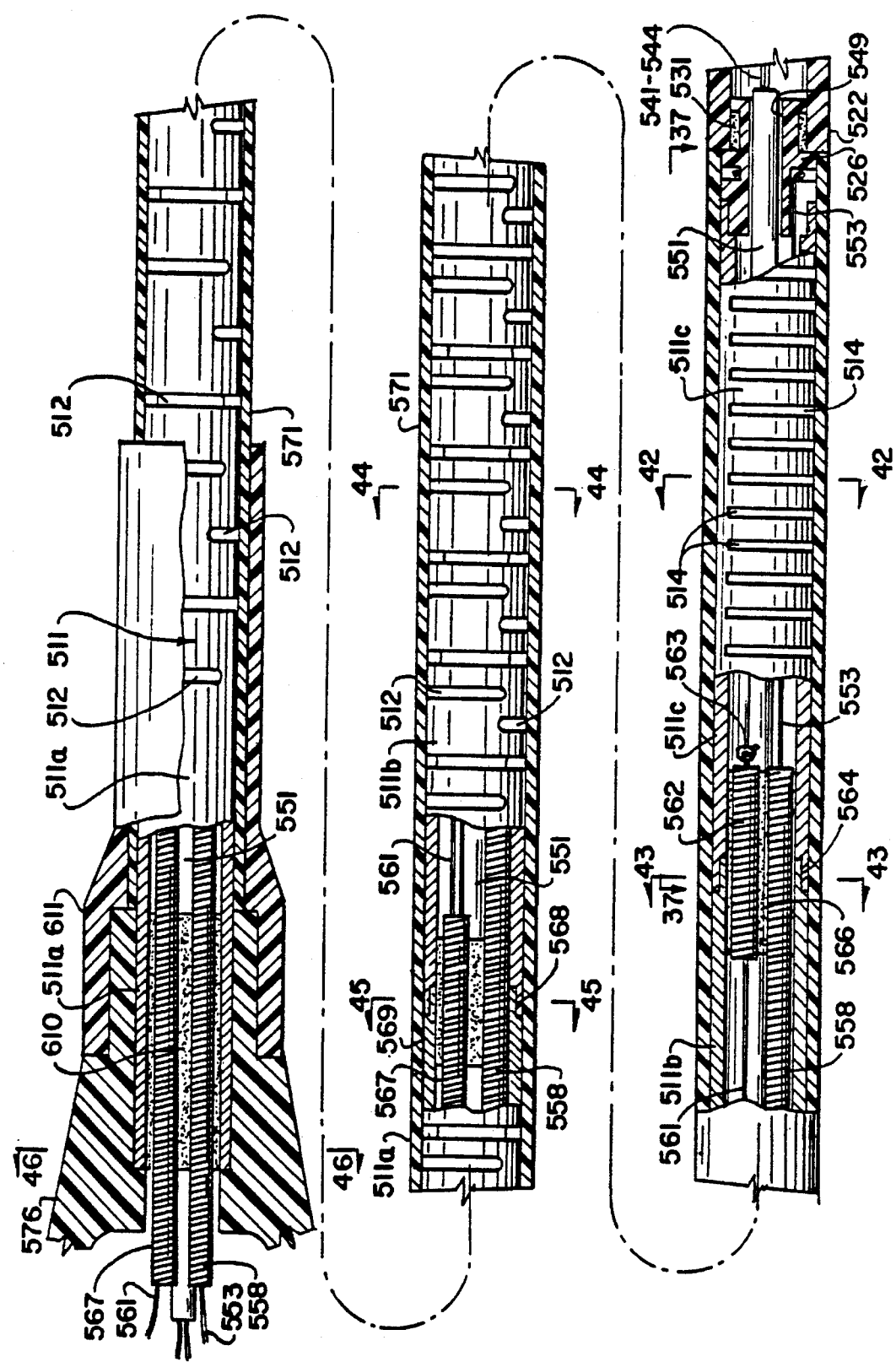
FIG. 36 is an enlarged cross-sectional view of a portion of the catheter as shown in FIG. 35.

The main torque tube portion or section 511a can have a suitable length as for example 38 inches and can be formed of a suitable material such as 13 gauge thin-wall stainless steel as hereinbefore described. It is formed in the matter hereinbefore described in connection with the previous embodiments and as shown particularly in FIG. 36 is provided with a plurality of longitudinally spaced apart slots 512 which extend through the cylindrical wall of the torque tube section 511a and which are radially offset with respect to each other as hereinbefore described.

Section 511b is similarly provided with such longitudinally spaced apart slots 512 extending radially through the wall but which are spaced closer together, as for example approximately one-half the spacing of the slots 512 provided in the section or portion 511a.

Figure 37:
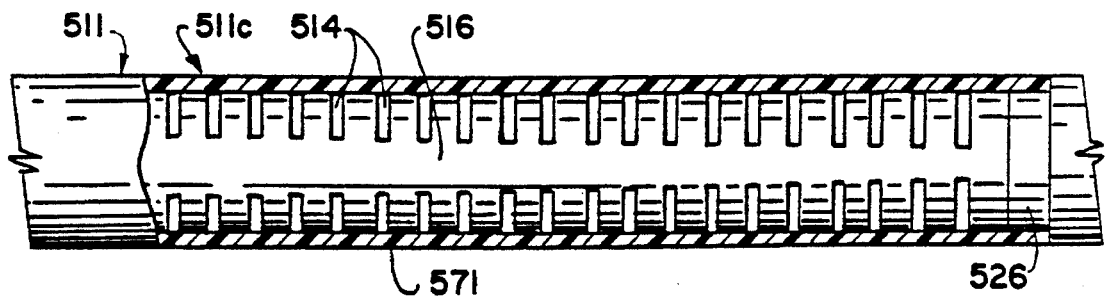
FIG. 37 is a cross-sectional view of the distal extremity of the catheter shown in FIG. 35 and shows a taper being provided in the integral rib of the catheter to provide varying degrees of flexibility in the bending of the distal extremity of the catheter.
Figure 38:
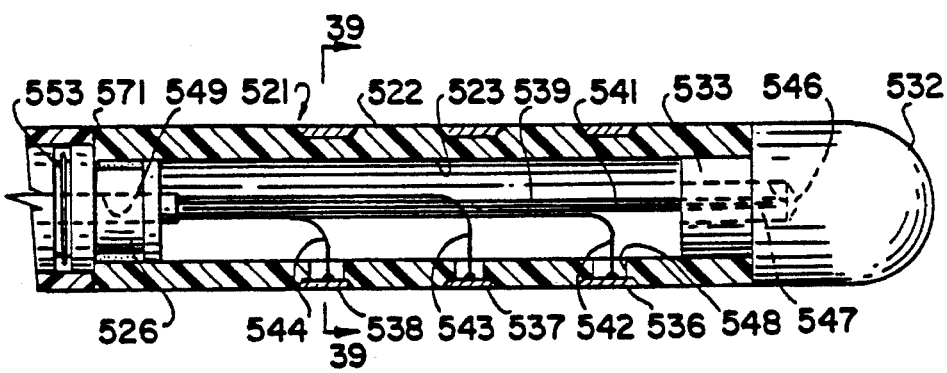
FIG. 38 is an enlarged cross-sectional view of the distal extremity of the catheter shown in FIG. 35.
Figure 39:
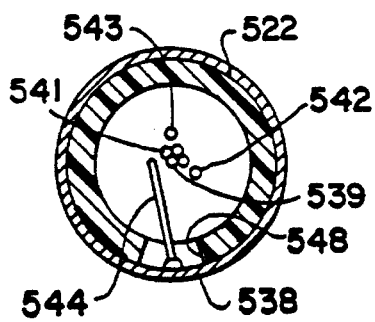
FIG. 39 is a cross-sectional view taken along the line 39—39 of FIG. 38.
Figure 40:
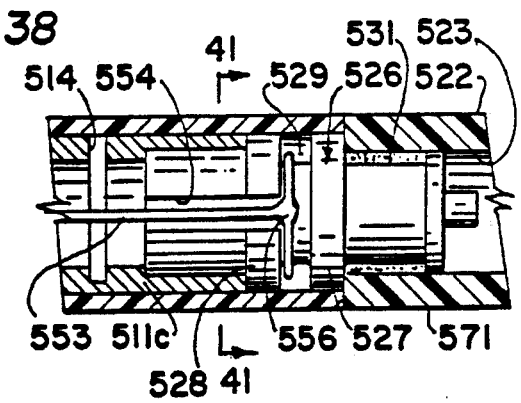
FIG. 40 is an enlarged cross-sectional view of a portion of the distal extremity of the catheter shown in FIG. 35.
Figure 41:
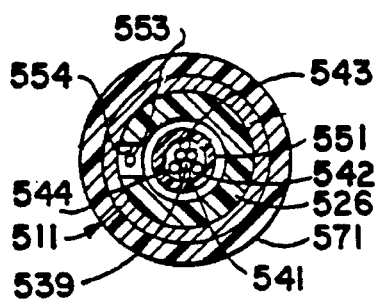
FIG. 41 is a cross-sectional view taken along the line 41—41 of FIG. 40.
Figure 42:
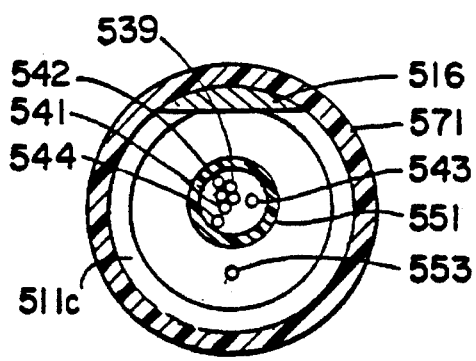
FIG. 42 is a cross-sectional view taken along the line 42—42 of FIG. 36.
Figure 43:
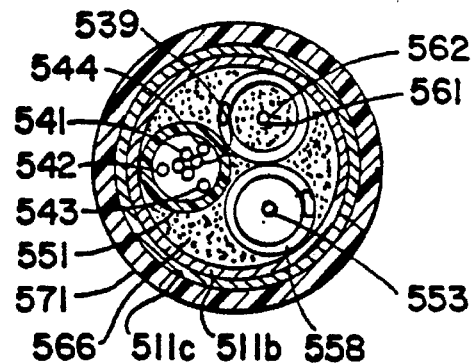
FIG. 43 is a cross-sectional view taken along the line 43—43 of FIG. 6.
Figure 44:
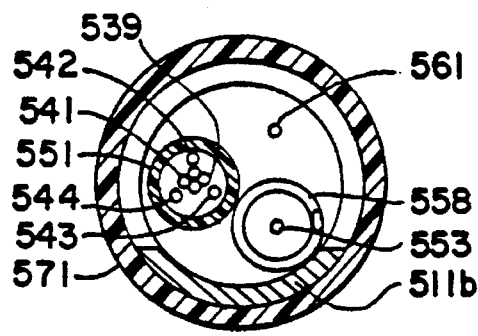
FIG. 44 is a cross-sectional view taken along the line 44—44 of FIG. 36.
Figure 45:
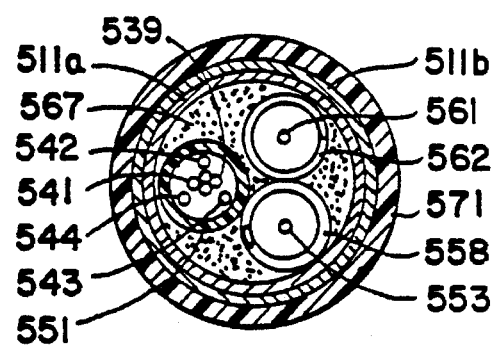
FIG. 45 is a cross-sectional view taken along the line 45—45 of FIG. 36.
Figure 46:
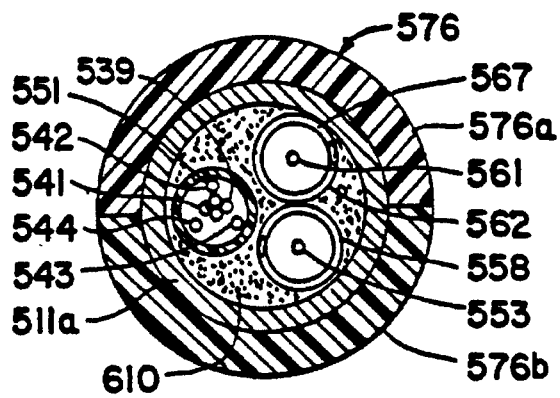
FIG. 46 is a cross-sectional view taken along the line 46—46 of FIG. 36.

Section 511c is provided with longitudinally spaced apart slots 514 also extending radially through the cylindrical wall of the section 511c. However, in this case, the slots 514 rather than being offset radially as are the slots 512, are not offset radially and extend substantially all the way through the circular tube except for a thin-wall portion (see FIG. 37) which serves as a rib or backbone 516. This rib or backbone thin-wall portion 516 serves to keep the section 511c unitary and also ensures that the bending in the section 511c as hereinafter described will only bend or curve in a plane which is at right angles or perpendicular to the plane of the backbone or rib 516. In order to provide different degrees of flexibility in this tip section 511c, the depths of the slots 514 can be varied so as the slots 514 become deeper, the backbone or rib 516 becomes narrower to permit greater flexibility in the backbone or rib 516, and conversely if the slots are shallower, the backbone or rib 516 will become wider to provide lesser flexibility. Thus as shown in FIG. 37 the backbone or rib 516 is tapered in a direction towards the distal extremity to provide gradually increasing flexibility toward the distal extremity.

It should be appreciated that if desired additional sections 511c could be provided in which the backbone or rib 516 could be offset radially with respect to the backbone or rib of the other section so as to obtain bending in different directions. As for example one backbone or rib 516 could be offset by 90° with another backbone or rib 516 to permit one section to bend in a direction at 90° offset from the bending of the other section.

Although the tip section 511c has been described as being formed out of a suitable metal such as No. 304 stainless steel with a 13 gauge wall thickness, it also can be made of a superelastic material known as a nickel titanium alloy, such as TINEL, hereinbefore described, which has greater capabilities of returning to the original or straight position than does stainless steel.

A tip piece 521 is mounted on the distal extremity of the torque tube 511 and consists of a tubular member 522 formed of a suitable insulating material such as plastic, as for example polyamide, which is provided with a central passage 523. One end of the tubular member 522 is mounted on one end of the fitting 526 and also is formed of a suitable material such plastic which is provided with two spaced apart radially-extending flanges 527 and 528 to provide an annular recess 529 between the same. It is secured to the distal extremity of the fitting 526 by a suitable means such as adhesive 531 (see FIG. 40).

A hemispherical or rounded platinum tip of the type hereinbefore described serving as a radio frequency electrode 532 is secured to the distal extremity of the plastic tubular member 522 by suitable means such as an adhesive. As can be seen from FIG. 38, the RF electrode 532 is provided with a cylindrical portion 533 of reduced diameter which is fitted within the passage 523 secured therein by an adhesive (not shown).

One or more ring electrodes can be provided on the tubular member 523 and as shown three of such ring electrodes 536, 537 and 538 have been provided which are spaced apart longitudinally of the tubular member 522. Wires 539, as for example three, formed of a suitable material such as stainless steel extend the length of the torque tube 11. Conductors 541, 542, 543 and 544 are provided for making electrical contact to the RF electrode 532 and to the ring electrodes 536, 537 and 538. Thus the conductor 541 as well as the three wires 539 extend into a bore 546 provided in the RF electrode 532 and are soldered therein by solder 547. The conductors 542, 543 and 544 extend through holes 548 provided in the tubular member 522 and are bonded to the ring electrodes 536, 537 and 538 in a suitable manner such as by spot welding. The conductors 541, 542, 543 and 544 in order to provide greater strength so that they can serve as safety wires in the same manner as wires 539 for preventing the tip piece 521 from being accidentally separated from the torque tube 511 are also formed of stainless steel to provide strength and are copper plated to provide the desired conductivity. The conductors 541, 542, 543 and 544 extend distally toward the distal extremity of the flexible elongate shaft 502 and extend through a bore 549 provided in the fitting 526. The conductors 541, 542, 543 and 544 are insulated from each other and from the wires 539 by suitable insulation (not shown) provided on the conductors. The wires 539 and conductors 541–544 are enclosed in a tubular member 551 formed of a suitable insulating material such as a suitable plastic, as for example polyamide. This tubular member 551 serves as a jacket for the wires 539 and conductors 541–544 and extends into a bore 549 of the fitting 526 (see FIG. 36). By way of example, the tubular member or jacket 551 can have a suitable outside diameter as for example 0.030" and an inside diameter of 0.025" so that there is adequate space for receiving the three wires 539 and the four conductors 541–544.

Means is provided for steering the tip section 511c of the torque tube 511 and consists of pull string 553 of a suitable material such as "KEVLAR" which has its distal extremity passing through a slot 554 provided in the fitting 526 and being tied about the fitting 526 within an annular recess 529 by tying a knot 556 in the "KEVLAR" string 553. So that its distal extremity is retained within the annular recess 529 is tied to the fitting 526.

The pull string 553 extends proximally from the fitting 526 within the section 511c outside the tubular member 551 (see FIG. 36) and extends into the distal extremity of a tubular coil spring 558 which extends into the distal extremity of the elongate flexible shaft 502. The coil spring 558 serves two purposes. It serves as a back-up spring for the bending of the tip section 511c. It also serves as a guide for the "KEVLAR" pull string 553. "KEVLAR" has been selected for the pull string 553 because it is a very strong, i.e., approximately the same as stainless steel. Also, it is more flexible and has less friction when it is moving within the coil spring back-up tube 558.

Another pull string 561 is provided also of "KEVLAR" which extends into a short length of coil spring 562. The pull string 561 is provided a knot 563 in its distal extremity to prevent it from being pulled through the coil spring 562. The coil springs 558 and 562 are held in place at a joint 564 by which the two sections 511b and 511c are joined together by a suitable adhesive 566 (see FIG. 3). As shown in FIG. 36, the pull string 561 extends from the short coil spring 562 within the interior of the torque tube section 511b which forms tractable or curved portion of the torque tube. The "KEVLAR" pull string 561 then extends into another coil spring 567 which extends to the proximal extremity of the elongate flexible shaft 502. The distal extremity of the coil spring 567 and the coil spring 558 are held in a fixed position at a joint 568 formed by joining the two sections 511a and 511b of the torque tube 511 by an adhesive 569. The coil spring 567 serves as a jacket for the pull string 561. It also serves as a back-up spring for the curve or tractable section 511b in the same manner as the coil spring 558 serves as a jacket for the pull string 553 and as a back-up for the tip section 511c.

Thus it can be seen that the two "KEVLAR" pull strings 553 and 561 extend to the proximal extremity of the elongate flexible shaft 502 and are separated from each other by the coil springs 558 and 567 to prevent the "KEVLAR" pull strings from rubbing against each other and from becoming entangled with each other. Thus, the coil springs 558 and 567 serve to reduce the friction of the pull strings 553 and 561 in their movement longitudinally of the elongate flexible shaft 502 and into the handle 502. Since the "KEVLAR" pull strings 553 and 561, as well as the coil springs 558 and 567, are very flexible, they will readily conform to the desired shape for the catheter without having a tendency to try to return the torque tube 511 to the original and straight shape. Also, by providing a portion of the pull string 553 which is free within the tip section 511c of the torque tube and a portion of the pull string 561 which is free or is not jacketed by a coil spring in the tractable or curved portion third section 511b of the torque tube, bending of the torque tube 511 in small radii can be caused to occur only in those regions as hereinafter explained.

As in previous embodiments of the invention, the torque tube 511 is encased within a shrink tube 571 of the type hereinbefore described, which extends from the proximal extremity to the distal extremity of the torque tube 511. In order to ensure that no sharp edges remain which could possibly puncture the shrink tube 571, it may be desirable to electropolish the torque tube 511 in a manner well known to those skilled in the art. It has been found that this is particularly desirable to remove burrs and sharp edges where the torque tubes have been fabricated by EDM technology.

As hereinbefore explained, the proximal extremity of the elongate flexible shaft 502 is mounted in a handle 506. The handle 506 consists of a housing 576 formed of a suitable material such as plastic which is comprised of two parts 576a and 576b which are adapted to be fastened together by suitable means such as an adhesive or by ultrasonic welding. As with the previous handle 91 hereinbefore described, the housing 576 is formed so it is adapted to readily fit within a human hand for use of the same in using the torquable catheter 501 as hereinafter described. Thus, housing 576 is provided with a proximal extremity 577 which is adapted to be engaged in the palm of the hand to permit collars 578 and 579 to be engaged by the fingers of the same hand holding the proximal extremity 577.

Figure 47:
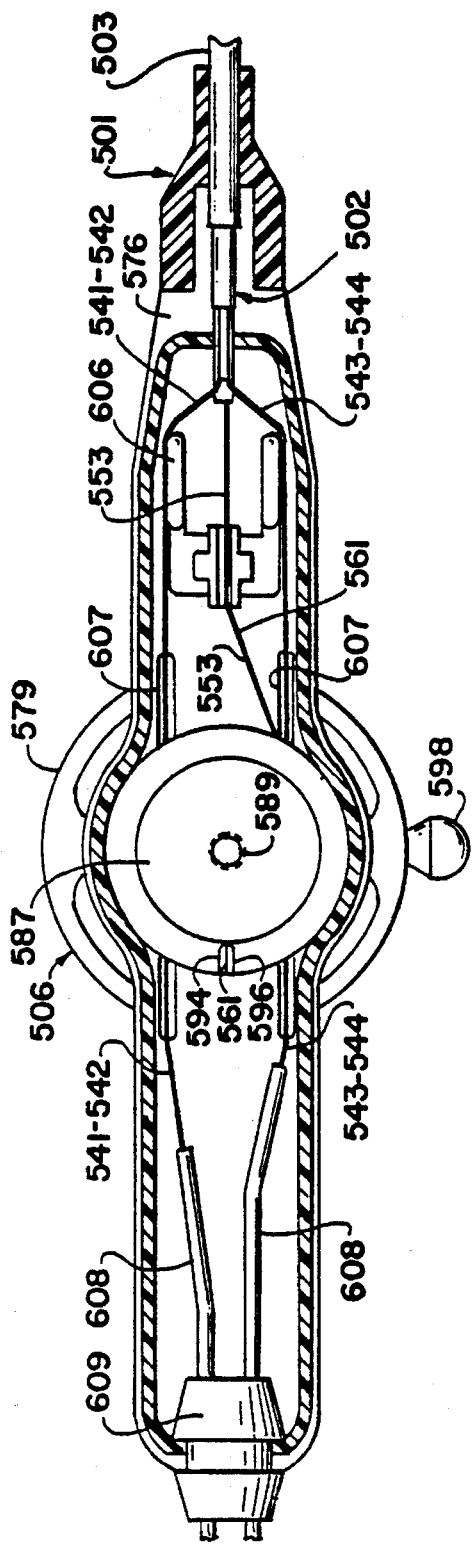
FIG. 47 is a cross-sectional view of the handle of the catheter shown in FIG. 35 as taken along the line 47—47 of FIG. 50.

The collars 578 and 579 are mounted upon knobs 581 and 582. The knobs 581 and 582 have cylindrical protrusions 583 which extend through holes 584 provided in the collars 578 and 579. The collars 578 and 579 can be secured in any desired rotational position with respect to the knobs 581 and 582, respectively, by set screws 586. The knobs 581 and 582 are movably secured to capstans 587 and 588 in a similar manner as, for example, by Phillips-head screws 589, which extend into a cylindrical protrusion 591, provided on the capstans 587 and 588 which extend through holes 592 provided in the housing parts 576a and 576b. The capstans 587 and 588 are provided with radially-extending flanges 593. The capstans 587 and 588 have the pull strings 561 and 553, respectively, secured thereto by wrapping the same around the capstans as shown (see FIGS. 49 and 50). The proximal extremities of the pull strings are secured to the capstans 587 and 588 in a suitable manner. For example, as shown in FIG. 47, the proximal extremity of pull string 553 is secured in the recess 594 by an adhesive 596.

The collars 578 and 579 are provided with protrusions 598 and 599, respectively, which are provided with threaded portions 598a and 599a threaded into the collars 578 and 579.

Protrusion 598 is hemispherical in shape, whereas protrusion 599 is cylindrical and of a substantially smaller size so that, the user of the torquable catheter 501 can readily ascertain which of the knobs 581 and 582 is being engaged by the finger of the hand.

O-rings 601 are provided between the housing 576 and the knobs 581 and 582 to form a liquid-tight seal between the same to help to ensure that liquids cannot enter the interior of the housing 576. Friction washers 602 are provided on the exterior of the housing 506 and engage similar friction washers 603 mounted on the underside of the knobs 581 and 582.

Figure 48:
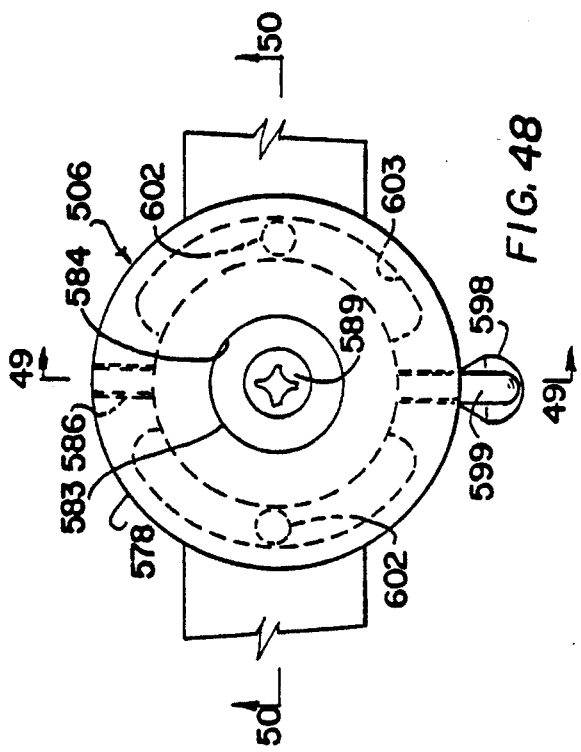
FIG. 48 is a top plan view looking along the line 48—48 of FIG. 49 showing a portion of the handle shown in FIG. 47.
Figure 49:
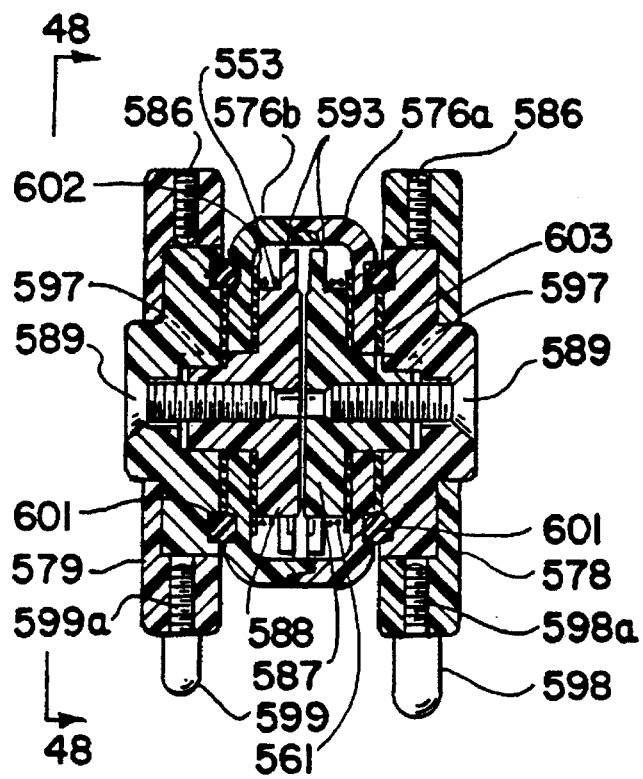
FIG. 49 is a cross-sectional view taken along the line 49—49 of FIG. 48.
Figure 50:
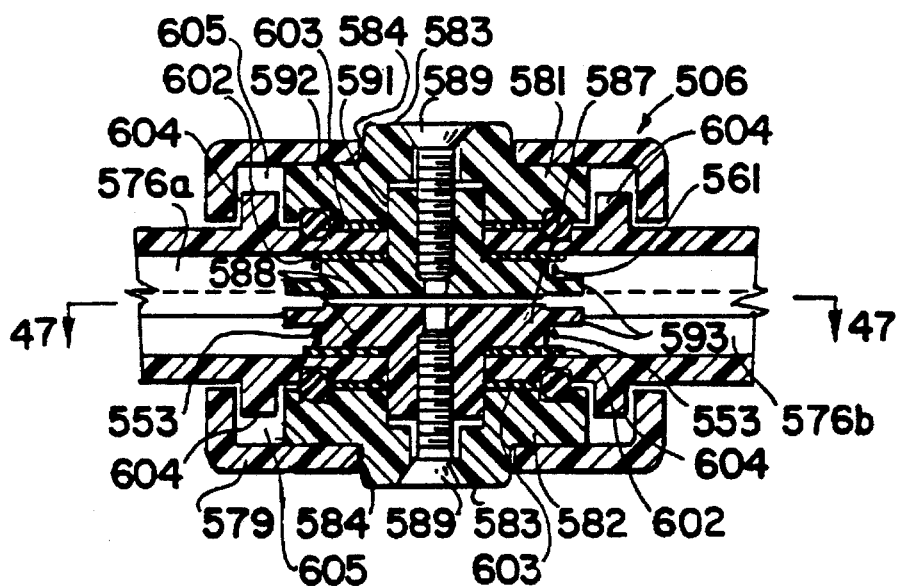
FIG. 50 is a cross-sectional view taken along the line 50—50 of FIG. 48.
Figure 51:
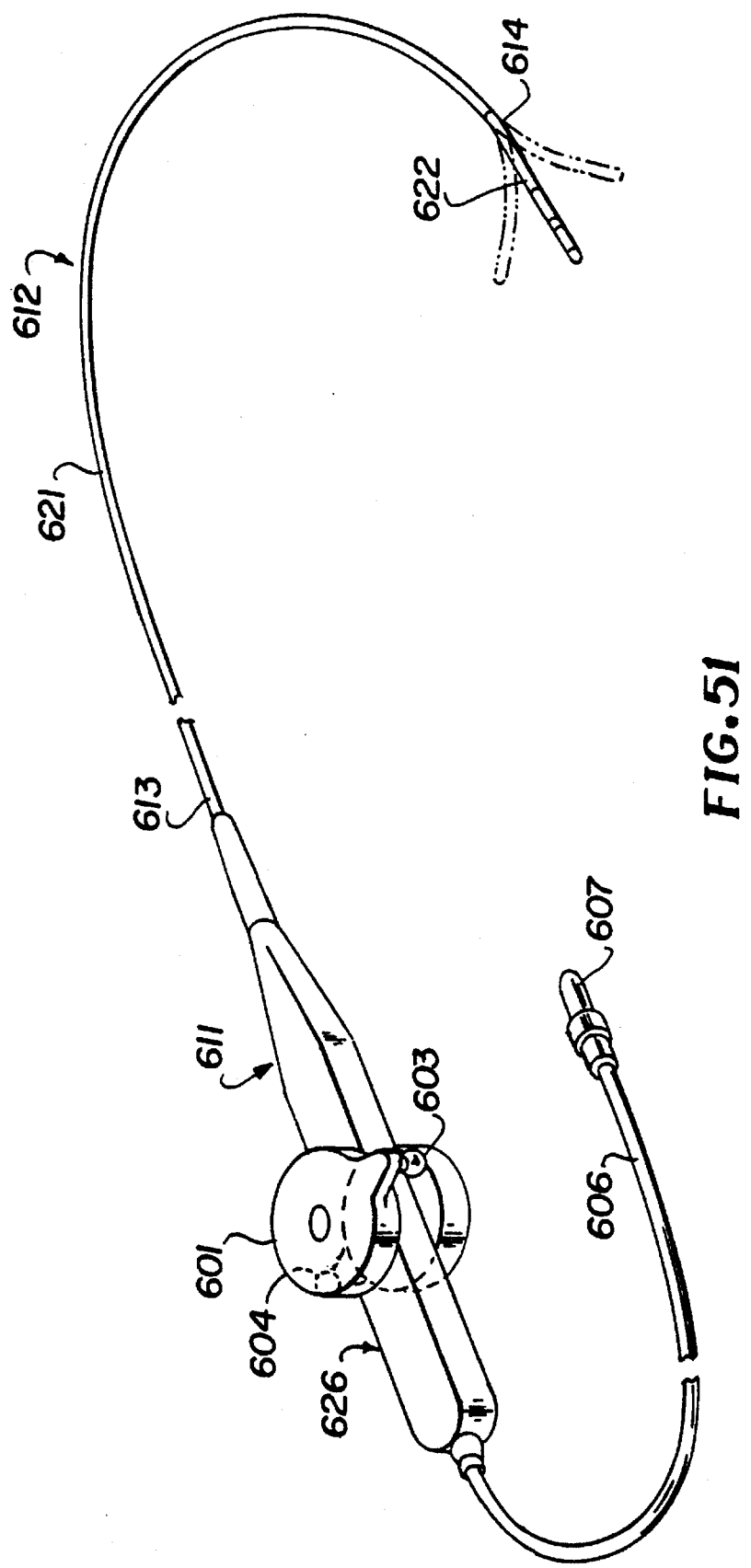
FIG. 51 is an isometric view of a torquable catheter incorporating the present invention.

Means is provided for permitting limited rotation of each of the capstans 587 and 588. As shown in FIGS. 48 and 50, this rotation limiting means takes the form of a pair of upstanding pins 604 which are provided on opposite sides of the housing and formed integral with the housing. These pins 604 extend into arcuate recesses 605 provided on opposite sides of the collars 578 and 579 (see FIG. 48) to permit limited rotation as, for example, 120° of the collars 578 and 579 relative to the housing 576.

As can be seen in FIGS. 47, the pull strings 553 and 561 extend from the proximal extremity of the flexible elongate shaft 502 and extend through a U-shaped fitting 606 mounted within the housing 506 and then travel proximally with respect to the capstans 587 and 588 and are secured thereto in a manner hereinbefore described. The conductors 541–544 also extend to the proximal extremity of the flexible elongate shaft 502 and are divided into two sets of conductors which travel around the U-shaped fitting 606 and pass over guides 607 provided within the housing 576 so they remain out of contact with the capstans 587 and 588. The conductors 541–544 then extend through flexible plastic tubes 608 that extend through a grommet 609 mounted in the proximal extremity of the housing 576. This can be seen from FIG. 36.

The proximal extremity of the elongate flexible shaft 502 is mounted within the distal extremity of the housing 576 and secured therein by suitable means such as an adhesive. A shrink fit cylindrical tube 611 is mounted on the distal extremity of the housing 576 and extends over the proximal extremity of the elongate flexible shaft 502 as shown in FIG. 36.

Operation and use of the torquable cathode 501 shown in FIGS. 37–50 may now be briefly described as follows. Let it be assumed that it is desired to adjust the handle 506 for the maximum bend which can be placed in the tip section 511c and in the tractable or curve section 511b. This adjustment is accomplished outside of the human body while observing the distal extremity of the torquable cathode 501. Let it be assumed that it is desired to place a desired bend in the tractable or curve section 511b. This is accomplished by holding the catheter 501 in one hand and holding the tractable section 511b in the other hand and grasping the tractable section 511b between two fingers of the other hand and placing a curvature or bend in the direction desired. This section 511b is tractable or malleable and retains at least a portion of the curvature or bend placed in the same primarily because of the stainless steel wires 539 and the conductor wires 541–544 which are present within that section and have a tendency to retain that shape. Thus, a preform is placed in the section 511b. Thereafter, the knob 581 carrying the collar 578 and the hemispherical protrusion 598 are rotated to cause a pulling force to be applied to the pull string 561 which causes a pulling force to be applied to the coil spring 562 anchoring the distal extremity of the pull string 561 to cause further bending to occur in the direction of the preform already established utilizing the distal extremity of the coil spring 567 as the back-up spring. Rotation of the knob 581 is continued until the maximum desired curvature is placed in the tractable section 511b. Because of the frictional engagement between the washers 602 and 603 associated with the knob 581, the knob will be retained in this position. The amount of friction which can be provided by the washers 602 and 603 can be readily adjusted by tightening or loosening the Phillips-head screw 589 which causes axial adjustment of the knob and the capstan relative to the housing 576.

After a maximum bend has been placed in the tractable section 511c, the set screw 586 is unscrewed to release the collar 578 from the knob 581. The collar is then rotated so that it abuts one end of the slot 605. The set screw 586 is then threaded inwardly to secure the collar 578 to the knob 581.

A similar procedure can be utilized for the tip section 511c. The collar rotated sufficiently far until a maximum bend is provided in the tip. The set screw 586 in the collar 579 is then unscrewed to permit rotation of it relative to the knob 582. The collar 579 is then moved until the extremity of the recess 605 is engaged by the pin 604. The set screw 586 is then tightened to secure the collar 579 to the knob 582 to thus provide the maximum excursion for the tip section 511c.

Figures 35, 35A:
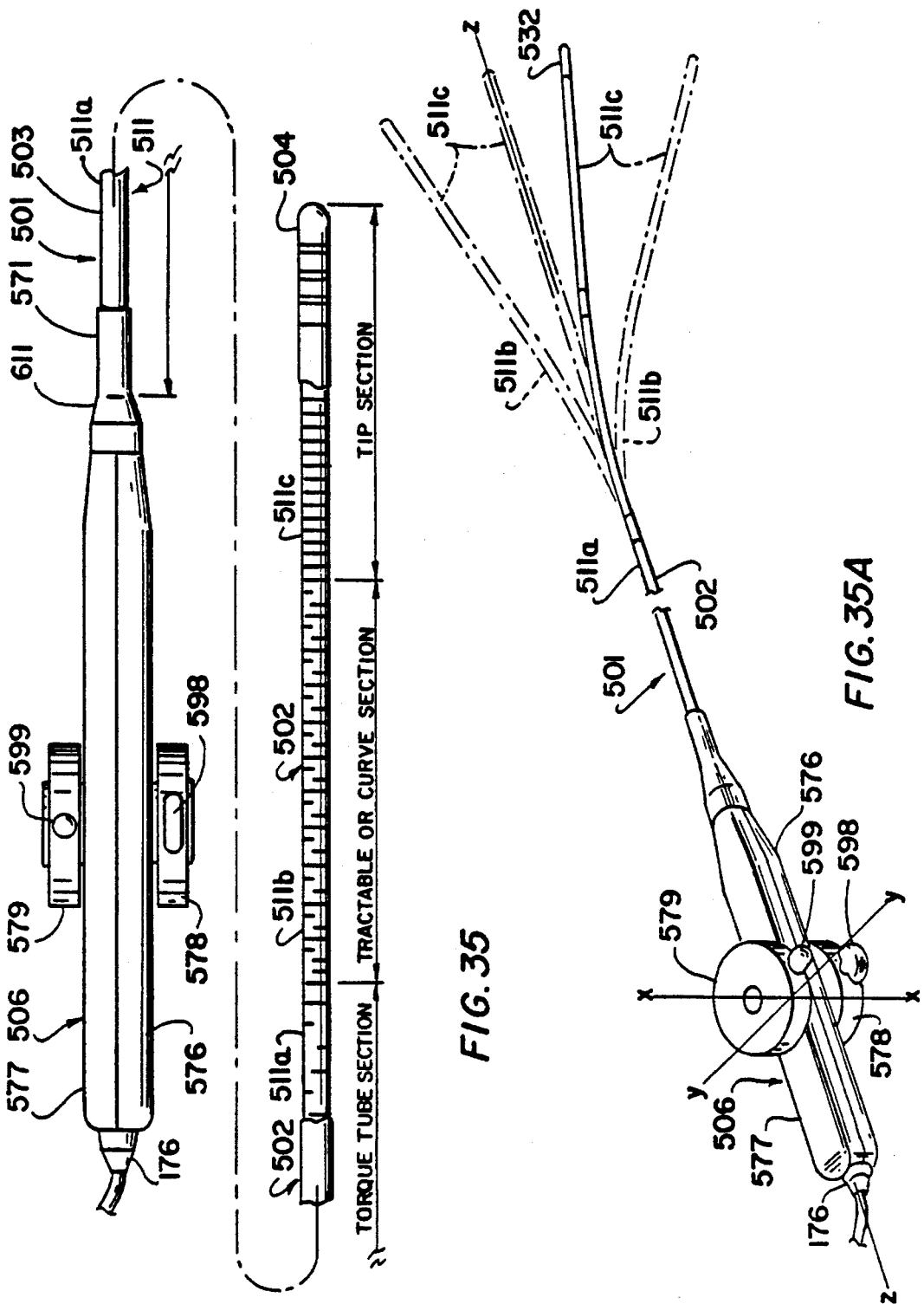
FIG. 35 is a side elevational view of another embodiment of a torquable catheter incorporating the present invention with portions of the same being shown in cross-section.
FIG. 35A is an isometric view showing the manner in which the tractable portion of the catheter can be preformed before introduction into a patient.

Let is be assumed that the torquable catheter 501 has been adjusted in the manner hereinbefore described and that it is desired to utilize the same in a mapping and/or ablation procedure. Assuming that the elongate flexible shaft 502 is in a straight position, a slight bend is provided in the tractable section 511b of the distal extremity of the elongate flexible shaft 502 as, for example, by grasping the handle 506 in the left hand and then using the thumb and the forefinger of the right hand and engaging the tractable section 511b to place a slight curve in the same as hereinbefore described as shown by the dotted line portions of section 511b in FIG. 35A. This slight bend or preform can be placed in the section 511b in any direction extending through 360° of rotation about the Z-axis as shown in FIG. 35A. In making this bend at the tractable section 511a, it is important to make the bend in the desired angle since this section 511b is tractable, in other words, is malleable and it will retain at least some of this bend after it is released by the fingers of the hand.

Thereafter, after the desired slight bend or preform has been provided in the tractable section 511a, the catheter can be introduced into the heart of the patient in the manner hereinbefore described in connection with the previous embodiments. After the distal extremity of the catheter 501 is in the desired position, the bend in the prebend provided in the tractable section 511b can be increased by operation of the appropriate knob 578 on the handle 506. The physician watching the distal extremity on the screen provided during fluoroscopy can continue to watch the screen without removing his eyes from the screen and merely feel the protrusions 598 and 599 to determine which knob he desires to operate. Since it is desired to operate the knob 578 to increase the bend in the tractable section 511b, the finger of the hand is used to sense the large hemispherical protrusion 598 indicating that this is the proper collar to be rotated. As shown, the collar 578 is rotated in the counterclockwise direction to cause further bending of the tractable section 511a. The direction of bend is determined by the prebend previously placed into the tractable section 511b before the catheter was introduced into the vessel of the patient. The physician by watching the screen can ascertain the amount of additional bend obtained by rotation of the collar 578 and the knob 581 associated therewith to achieve a desired bend up to the maximum bend achievable. These types of bends are shown in FIG. 35B.

Let it now be assumed that it is desired to place a bend in the section 511c. As hereinbefore explained, the tip section 511c can only be bent a plane because of the thin-wall portion providing a backbone or rib 516 provided in this section. The tip of the elongate flexible shaft 502 is positioned so that the backbone rib 516 lies in a plane which is perpendicular to the plane of the handle extending diametrically across the X-axis as defined by the centers of rotation for the collars 578 and 579. Since the physician knows this is the case, by controlling the rotational position of the handle 506 along the Z-axis, the physician selects the plane in which the tip section 511c is to be bent. After this plane has been selected, the collar 579 with its associated knob 582is rotated as, for example, in a counterclockwise direction by the physician feeling the protrusion 599 and ascertaining that is the knob 582 which is to be rotated for causing bending of the tip section 511c. Rotation of the same in a clockwise direction causes movement of the tip section 511 to form a bend as shown in FIG. 35C which can extend up to and beyond approximately 180°. As shown in FIG. 35C, this tip section 511 can lie in various planes at different angular positions about the Z-axis by merely rotating the handle 506 about the Z-axis.

Thus, it can be seen that by providing an intermediate tractable section 511b in which a preform can be provided extending through 360° of the Z-axis and by providing a tip section, although it can only be bent in a plane determined by the positioning of the backbone or rib portion 516, it is possible to locate the tip piece 521 in any region of the heart. This is accomplished by appropriate rotation of the handle 506 and by placing a predetermined bend in the preform of tractable section 511b and another bend in the tip section 511c by rotation of the knobs 581 and 582.

It can be seen with a torquable catheter 501 having such capabilities, it is possible to perform very precise mapping and ablation procedures which can be very selective with respect to the walls of the heart chamber being mapped and/or ablated. The mapping and ablation procedures can be carried out in a manner hereinbefore described in conjunction with the previous embodiments.

By placing the pull strings 553 and 561 in coil springs, it is possible to greatly reduce the friction making it possible for such pull means to extend through the relatively long length of shaft of the catheter. By anchoring the strings and placing appropriate support back-ups, it is possible to precisely to determine which sections of the elongate flexible shaft 502 will be bent by the pull strings.

Another embodiment of a torquable catheter incorporating the present invention is shown in FIGS. 61–62. It is also disclosed in copending application Ser. No. 07/945,512, filed Sep. 16, 1992 (A-56825). The torquable catheter 611 of the present invention consists of a flexible elongate tubular member 612 having proximal and distal extremities 613 arid 614, and having a longitudinal axis (not shown) extending through the same.

The flexible elongate tubular member 612 can have a suitable length depending upon the use for which the catheter is to be utilized. For example, if it is to be utilized for performing ablation procedures in the human heart it can have a length ranging from 130 to 150 cm. With such a length, the plastic tube portion 621 can have a length from 100 to 120 cm. The plastic tube portion 621 is formed of a reinforced plastic tube 631 such as supplied by Burnham Polymeric, Inc. of Glen Falks, N.Y. 12801, which is available commercially as a "Bi-Helix" (trademark) tube. The tube is available in various sizes, as for example 6 to 8 French. If an 8 French tube is utilized, such a tube has an outside diameter of 0.105 inches and an inside diameter of 0.082 inches, to provide a wall thickness of 0.0115 inches. Such a Bi-Helix tube is formed of a suitable plastic such as "PEBAX". In order to make it visible under X-ray, it can be provided with 20% barium sulfate filler. Reinforcing is provided in the Bi-Helix (trademark) tube by stainless steel wires having a diameter of 0.002 inches. Eight such stainless steel wires are wound as separate layers in tube 631. The wires are counterwrapped in two different spirals to provide the desired torque characteristics. The "PEBAX" plastic material utilized had a Shore hardness of 72D and can range from 25D to 90D.

The tube 631 is provided with a central lumen 632 extending the length thereof and in which there are disposed three elongate guide spring coils 636, 637 and 638 all of which extend from the proximal extremity 613 of the tubular 612.

The metal torque tube portion 622 is similar to that described in co-pending application Ser. No. 07/790,648 filed Nov. 8, 1991. As shown in FIG. 2, the metal torque tube portion 622 is comprised of a metal torque tube 639 having three sections 641, 642 and 643. All of the sections 641, 642 and 643 are formed of stainless steel tubing or preferably of a superelastic material such as "TINEL" of a suitable size and length. For example, with an 8 French Bi-Helix tube utilized for the plastic tube portion 621, the metal torquable tube 639 would have an outside diameter of 0.095 inches and an inside diameter of 0.077 inches with a wall thickness of 0.009 inches. The sections 641, 642 and 643 can have suitable lengths depending upon the application. For example, the section 641 can have a length of 3.1 inches and ranging from 2 to 4 inches. The section 642 can have a length of 0.6 inches, but can range in length from 0.5 to 2 inches. The section 643 can have a suitable length such as 2.175 inches and can range in length from 1 to 3 inches. Thus, the sections 641, 642 and 643 can have an overall combined length of 6.1 inches.

The sections 641, 642 and 643 are provided with at least one and preferably a plurality of slots, respectively slots 647, 648 and 649 respectively which extend transversely of the longitudinal axis of the flexible elongate tubular member 612 and which are spaced longitudinally of the longitudinal axis. Each of the slots subtends an angle of less than 360°. The slots 647, 648 and 649 have a suitable width, as for example 0.0250 inches with the intervening wall between the slots having a thickness of 0.0250 inches. The slots 647 in the section 641 subtend and angle of 300° and are radially offset 120° with respect to each other (see FIGS. 55–57) so that every fourth slot extending longitudinally has the same radial offset. The slots 648 in the section 642 subtend angles of 300° with every other slot 648 being offset radially by 180° to provide ribs 651 and 652 extending longitudinally of the section 642. The slots 649 in the section 643 subtend an angle of 300° and are aligned radially but are offset with respect to the slots 648 in the section 641 by an angle of 90°. Thus, a rib 653 extends longitudinally of the section and of the longitudinal axis of the flexible elongate tubular member 612.

Spaced apart elongate windows 656 and 657 are provided in the metal torque tube 639 and extend longitudinally of the longitudinal axis of the flexible elongate tubular member 612.

Means is provided for interconnecting the metal torque tube portion 622 to the plastic tube portion 621 and consists of a joint or transition 661. The joint or transition 661 is formed by turning down the proximal extremity of the section 639 which is in the form of an unslotted portion 662 to provide a portion 663 which has a reduced diameter of 0.0082 inches so that it slides into the distal extremity of the plastic torque tube portion 621 and is secured therein by a suitable means such as an adhesive (not shown).

The guide coil springs 636, 637 and 638 as well as insulating tube 634 extend through the centrally disposed passage 664 provided in the section 641 and extend into the window 656. The guide coil springs 636 and 638 terminate at the distal extremity of the window 656 and are retained in a fixed position by suitable means such as an adhesive (not shown). The same adhesive is utilized for securing the guide coil spring 637 and insulating tube 634 within the window 651. "KEVLAR" pull lines 666 and 667 are slidably mounted in the guide coil springs 636 and 638 and are connected to the handle 626 in a manner herein before described in co-pending application Ser. No. 07/790,648, filed Nov. 8, 1991. The "KEVLAR" pull lines 666 and 667 extend distally from the window 656 through the central passage 664 in the section 642 then to the window 657 provided between the sections 642 and 643. The "KEVLAR" pull lines 666 and 667 extend through notches 668 and 669 provided on opposite sides of a first or proximal curve anchor 671 (see FIG. 60) which is disposed in the window 657. Knots 672 are tied into the distal extremities of the "KEVLAR" pull lines 666 and 667 are sized so that they cannot be pulled back through the notches 668 and 669. In addition, the distal extremities of "KEVLAR" pull lines 666 and 667 are retained within the anchor 671 by suitable means such as adhesive (not shown) securing the pull lines within the notches 668 and 669.

The guide coil spring 637 also extends through the central passage way 664 provided in the section 643 and terminates at the proximal extremity of the anchor 671. It is retained in this position by use of the adhesive (not shown) provided in the window 657 for securing the pull lines 666 and 667. The "KEVLAR" pull line 673 is similar to the pull lines 666 and 667 is provided within the guide spring coil 637 and is secured to the handle 626 and extends distally of the anchor 671 and extends through the central passageway 664 of the section 643. The distal extremity of the Kevlar pull line 673 is secured to a second or distal curve anchor 674 and mounted in the distal extremity of the section 463.

The first and second anchors 671 and 674 can be formed of a suitable material such as plastic. The second or distal curve anchor 674 is provided with cylindrical portion 674a of reduced diameter which fits within the distal extremity of the section 643 and is seated within the central passageway 664. It is also provided with the centrally disposed portion 674b of reduced diameter in the form of a angular slot the distal extremity of the "KEVLAR" pull line 673 extends distally through a slot 675 provided in the anchor 674. The distal extremity of the "KEVLAR" pull line 673 is provided with a loop 673a which is looped around the portion 674b of reduced diameter and then knotted of 673b. The loop 673 can also be secured in by suitable means such as an adhesive (not shown).

The insulating sleeve 634 extends up to the second or distal curve anchor 674. The insulating sleeve 634 is provided with a pair of insulated electrical conductors 676 and 677 therein which extend centrally through the second or distal curve anchor 674 (see FIG. 62).

An elongate flexible sleeve 686 extends over and encloses the sections 641 and 642 of the metal torque tube portion 622. As shown in the drawings, it has an outer diameter which is the same as the outer diameter of the plastic torque tube portion 621 so that there is a smooth transition at the joint between the plastic torque tube portion 621 and the metal torque tube portion 622. Thus, with the 8 French Bi-Helix tube having an outside diameter of 0.105 inches, the sleeve 686 also has an outside diameter of 0.105 inches and has a wall thickness of 0.005 inches so that it can enclose the metal torque tube portion 622 and still provide the flush connection between the portions 621 and 622. This sleeve 686 can be formed of a suitable material such as a heat-shrinkable polyolefin. The sleeve 686 serves as a protective cover to prevent blood and other body fluids from entering into the slotted torque tube while still permitting the desired bending of the torque tube.

The flexible elongate tubular member 612 also includes a tubular plastic section 691 at the distal extremity of the flexible elongate tubular member 612. The tubular plastic section 691 can be formed of a suitable plastic material such polyurethane or "PEBAX", and can have a suitable length, as for example 1 cm. It has an exterior diameter of 0.105 inches so that it has the same external diameter as the remainder of the flexible elongate tubular member 612. The tubular section 691 may be of 8 French size and has a suitable wall thickness, as for example 0.014". Alternatively, the tubular section 691 can be of smaller diameter such as 7 French. A rounded conducting tip 692 formed of a suitable material such as platinum is mounted on the distal extremity of the tubular plastic section 691 and secured thereto by suitable means such as an adhesive. A ring 693 also formed of a suitable conducting material such as platinum is mounted on and recessed in the tubular plastic section 691 proximally of the tip 692 and spaced from the tip 692. The exterior surfaces of the rounded tip 692 and the ring 693 are exposed but are flush with the cylindrical surface of the tubular section 691.

Means is provided for bonding the proximal extremity of the tubular plastic section 691 to the distal extremity of the section 642. This means consists of a flanged portion 674c of reduced diameter of the distal anchor 674 over which the proximal extremity of the tubular plastic section 691 is disposed and secured thereto by suitable means such as an adhesive (not shown).

The insulating tube 634 extends through the second anchor 674 and terminates one of the conductors 676 connected to the tip 692 by solder 698. The other of the conductors 677 is connected by solder 699 to the ring 693. The conductors 676 and 677 extend through the handle 626 and are connected through a flexible cable 706 to a connector 707 which is adapted to be connected to a power supply (not shown).

As pointed out previously, the handle 626 is in the form of a steering handle which is provided with steering wheels 701 and 702 mounted on opposite sides of the same and which are provided with knobs 703 and 704 for actuation of the same. Movement of the knob 703 causes movement of the "KEVLAR" pull lines 666 and 667 to cause bending of one portion of the flexible elongate tubular member 612 in either of two directions as determined by the ribs 651 and 652. Movement of the knob 704 causes movement of the Kevlar pull line 673 to cause bending of a more distal portion of the flexible elongate tubular member 612 in one direction as determined by the rib 653.

Operation and use of the torquable catheter 611 shown in the drawings may now be briefly described as follows. Let is be assumed that it is desired to utilize the catheter 611 in connection with a mapping and/or ablation procedure in a chamber of the heart to cause ablation of a portion of the wall forming a chamber of the heart. The catheter 611 can be advanced into the chamber of the heart in a conventional manner such as through the femoral artery of the patient. The physician while holding the steering handle 626 in one hand introduces the distal extremity of the catheter into the femoral artery of the patient and then advances the same into the chamber of the heart. The catheter has sufficient rigidity so that it can be pushed or advanced into the femoral artery while observing the same under a fluoroscope. This advancement is continued until the distal extremity of the catheter has been advanced into the desired chamber of the heart with the electrodes 692 and 693 in contact with or adjacent to a wall forming the chamber of the heart in which the distal extremity of the catheter is disposed. The mapping and/or ablation procedures can thereafter be carried out in a conventional manner, after which the catheter can be withdrawn.

The torquable catheter of the present invention in such a use has a number of advantages. The use of the plastic torque tube portion of the catheter makes the catheter very flexible throughout substantially its entire length. At the same time it makes the catheter susceptible to use in rather sharp bends without adversely affecting the characteristics of the torque tube while still retaining the capability of transmitting torque without twisting in a 1:1 ratio. The provision of the metal torque tube portion at the distal extremity of the catheter still maintains all of the desired steering capabilities for the catheter by making it possible to steer the distal extremity by use of the steering wheels 701 and 702 on the handle 626 to cause bending of the distal extremity of the catheter. Bending in any direction can occur in the torque tube section 641, bending in two directions in torque section 642 and in one direction in torque tube section 643 to positions the distal extremity of the catheter in the desired location. The catheter is constructed in such a manner so that it can be constructed economically.

Another embodiment of a torquable tubular member or torque tube for use in the torquable catheter 611 shown in FIGS. 51–62 is shown in FIGS. 63–65. The torquable tubular member or torque tube 711 is formed of a metal of the type hereinbefore described. By way of example, it can be formed of "TINEL". The torquable tubular member 711 is of the same general configuration as torquable tubular member 639 shown in FIGS. 51–62 with sections 641 and sections 642a and 643a, with the principal difference being that L-shaped slots 712 are formed in the section 642a and L-shaped slots 713 are formed in the section 643a of the tubular member which are spaced apart longitudinally of the tubular member 711 rather than the straight slots 648 and 649 provided in the torquable tubular member 639.

The L-shaped slots 712 and 713 can be formed in a suitable manner such as by EDM machining by a method and apparatus of the type disclosed in co-pending application Ser. No. 945,538, filed Sep. 16, 1992 (A-55920/HCH). As shown in the drawings, the L-shaped slots 712 and 713 are provided with first portions 712a and 713a respectively which extend radially of the torquable tubular member 711 and subtend an angle of less than 360°. The portions 712a and 713a are spaced apart longitudinally of the longitudinal axis of the torquable tubular member 711. The L-shaped slots 712 and 713 are also provided with second or leg portions 712b and 713b which extend at right angles to the first or straight portions 712a and 713a and in a direction which is parallel to the longitudinal axis of the torquable tubular member 711. These leg portions 712b and 713b extend in a direction proximal of the torquable tubular member 711 as shown in the drawings. However, it should be appreciated that if desired the leg portions 712b and 713b can extend in an opposite direction distal of the torquable tubular member. As shown in FIGS. 63 and 65, the L-shaped slots 712 are formed in the section 642a in positions which are offset by 90° with respect to the L-shaped slots 713 formed in the section 643a to impart flexibility in different directions as hereinbefore described. In the section 642a, every other slot is offset with respect to the other slot by 180°, to form the ribs 651 and 652 to permit bending in two different directions. It has been found that by providing a torquable tubular member 711 which has been provided with such L-shaped slots that the torquable tubular member is much more flexible in bending with respect to the ribs 651 and the ribs 652 provided in the section 642a. This greater flexibility is provided by removal of the additional material provided in forming the second or leg portions 712b of the slots 712 to permit improved flexing of the material in the rib. Similarly, the L-shaped slots 713 in the section 643a form a rib 653 to permit more flexible bending in a single direction.

By way of example, a torquable tubular member 711 constructed in the manner shown in FIGS. 63–65 had an outside diameter of 0.0950" and an inside diameter of 0.0770" to provide a wall-thickness of 0.009". The torquable tubular member 711 had a total length of 6.1" with section 641 having a length of 3.1" section 642a having a length of 0.0625" and section 643a having a length of 2.025" with the recesses 656 and 657 having a length of 0.125". The straight portions 726 of the slots 712 and 713 subtend angles of approximately 300° with the slots being spaced apart 0.050" longitudinally of the torquable tubular member 711, the width of the slots being 0.015" which are cut utilizing 0.012 wire in the EDM machine. The length of the leg portions 712b and 713b provide a slot length of 0.0345" so that there remains 0.0155" of material prior to commencement of the next slot.

Other embodiments of the invention within the scope of the present invention can utilize different electrode tip configurations to achieve desired diagnostic and pacing functions as well as mapping and/or ablation. In conjunction therewith radio frequency and microwave energy can be utilized when desired.

What is claimed is:

1. A torquable tubular member for use in a flexible elongate device comprising an elongate tubular body having a cylindrical wall and a longitudinal axis extending longitudinally of the cylindrical wall, said cylindrical wall having formed therein a plurality of slots spaced apart longitudinally of the longitudinal axis, at least certain of said slots having a first portion which extends generally circumferentially of the cylindrical wall of the elongate tubular body and a second portion which extends generally longitudinally of the cylindrical wall of the elongate tubular body.

2. A torquable tubular member as in claim 1 wherein said slots subtend angles of less than 360° to form a rib extending longitudinally of the body and wherein the second portions of each of said certain slots is in close proximity to the rib to provide increased flexibility to the torquable tubular member.

3. A torquable tubular member as in claim 1 wherein said body is formed of metal.

4. A torquable tubular member as in claim 3 wherein said metal is formed of a superelastic material.

5. A torquable tubular member as in claim 4 wherein said superelastic material is a nickel titanium alloy.

6. A torquable tubular member as in claim 1 wherein other of said plurality of slots have a first portion which extends generally circumferentially of the cylindrical wall of the elongate tubular body and a second portion which extends generally longitudinally of the elongate tubular body, said first portion of said other slots having a width extending longitudinally of the cylindrical wall, said second portion of said other slots having a dimension extending longitudinally of the cylindrical wall which is greater than the width of said other slots and wherein said other slots is offset circumferentially with respect to said at least certain of said slots.

7. A torquable tubular member as in claim 6 wherein other of said slots are offset circumferentially by approximately 90°.

8. A torquable tubular member as in claim 1 wherein said elongate tubular body is provided with first and second sections and wherein said spaced apart slots are provided in each of the sections.

9. A torquable tubular member as in claim 8 wherein a recess is formed in said body in between said first and second sections.

10. A torquable tubular member for use in a flexible elongate device comprising an elongate tubular body having a cylindrical wall having a length and having a longitudinal axis extending along the length of the cylindrical wall, said cylindrical wall having first and second sections, said cylindrical wall having a plurality of spaced-apart slots extending along the longitudinal axis of each of said first and second sections, said cylindrical wall being formed with a recess between the first and second sections, said slots having a width along the longitudinal axis, said recess having a width along the longitudinal axis which is substantially greater than the width of the slots, said slots and said recess being circumferentially aligned so that a rib is defined which extends longitudinally of the longitudinal axis.

11. A torquable tubular member as in claim 10 wherein said slots extend generally circumferentially of the cylindrical wall.

12. A torquable tubular member as in claim 10 wherein at least a portion of said cylindrical wall is formed of metal.

13. A torquable tubular member as in claim 12 wherein said metal is a superelastic material.

14. A torquable tubular member as in claim 13 wherein said superelastic material is a nickel titanium alloy.

15. A torquable tubular member as in claim 10 wherein at least certain of the slots in one of said first and sections is offset circumferentially with respect slots in the other of said sections.

16. A catheter having a high flexibility comprising an elongate flexible body having a length, a proximal end, a distal end and a longitudinal axis extending along the length of the elongate flexible body, the elongate flexible body including a cylindrical wall having a passage extending longitudinally of the cylindrical wall, at least a portion of which is formed of a metal and is adjacent the distal extremity, at least a portion of said cylindrical wall of metal having formed therein a plurality of slots spaced apart along the longitudinal axis, said slots subtending at angles of less than 360°, said slots imparting additional flexibility to said cylindrical wall of metal to permit bending about the longitudinal axis without permanent deformation of the metal, control means on the proximal end of the flexible elongate body and extending to the distal end of the body for transmitting a force to the distal end of the body to cause bending of said at least a portion of said cylindrical wall of metal having the slots therein.

17. A catheter as in claim 16 wherein said slots are substantially in circumferential alignment with each other and define a rib extending longitudinally of the longitudinal axis.

18. A tubular assembly comprising a tubular member having longitudinal axis and a cylindrical wall extending along the longitudinal axis, the cylindrical wall having at least a portion thereof having a plurality of L-shaped slots formed therein facing in the same direction and spaced apart longitudinally of the cylindrical wall along the longitudinal axis, each of said L-shaped slots subtending less than 360°, each of said L-shaped slots having a first portion having a width which extends generally circumferentially of the cylindrical wall and a second portion which extends generally longitudinally of the cylindrical wall beyond the width of the first portion, said L-shaped slots being aligned circumferentially and defining a rib extending longitudinally of the longitudinal axis and means connected to the tubular member for causing bending of the portion of the tubular member having the L-shaped slots therein.

* * * * *